US008975293B2

(12) United States Patent
Engel et al.

(10) Patent No.: US 8,975,293 B2
(45) Date of Patent: Mar. 10, 2015

(54) EPIGENETIC CO-REPRESSORS OF THE GAMMA-GLOBIN GENE AND METHODS OF USING SAME

(75) Inventors: James Douglas Engel, Ann Arbor, MI (US); Osamu Tanabe, Sendai (JP); Lihong Shi, Ann Arbor, MI (US)

(73) Assignee: Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 13/480,036

(22) Filed: May 24, 2012

(65) Prior Publication Data

US 2013/0059806 A1 Mar. 7, 2013

Related U.S. Application Data

(60) Provisional application No. 61/588,245, filed on Jan. 19, 2012, provisional application No. 61/490,175, filed on May 26, 2011.

(51) Int. Cl.
*A61P 7/00* (2006.01)
*A61K 31/708* (2006.01)
*G01N 33/68* (2006.01)
*G01N 33/80* (2006.01)

(52) U.S. Cl.
CPC ............ *G01N 33/6854* (2013.01); *G01N 33/80* (2013.01); *G01N 2333/91017* (2013.01); *G01N 2500/10* (2013.01)
USPC ................. 514/476; 514/34; 514/44 R; 435/8

(58) Field of Classification Search
CPC .............. G01N 33/80; G01N 2500/10; G01N 2333/91017; G01N 33/721
USPC ............................... 514/476, 34, 44 R; 435/8
See application file for complete search history.

(56) References Cited

U.S. PATENT DOCUMENTS

| 5,700,640 | A | 12/1997 | Voss et al. |
|---|---|---|---|
| 7,871,803 | B2 | 1/2011 | Takenaka |
| 7,892,791 | B2 | 2/2011 | Miyawaki et al. |
| 7,897,385 | B2 | 3/2011 | Miyawaki et al. |
| 7,910,714 | B2 | 3/2011 | Glick et al. |
| 7,939,649 | B2 | 5/2011 | Gambhir et al. |
| 2008/0008651 | A1 | 1/2008 | Engel |
| 2011/0251149 | A1* | 10/2011 | Perrine et al. ................ 514/43 |
| 2012/0207744 | A1* | 8/2012 | Mendlein et al. .......... 424/130.1 |

FOREIGN PATENT DOCUMENTS

| WO | WO 84/03564 | 9/1984 |
|---|---|---|
| WO | WO 91/18980 | 12/1991 |
| WO | WO 93/06121 | 4/1993 |
| WO | WO 94/08051 | 4/1994 |
| WO | WO 95/12608 | 5/1995 |
| WO | WO 95/30642 | 11/1995 |
| WO | WO 95/35503 | 12/1995 |

OTHER PUBLICATIONS

Cui et al. Nuclear Receptors TR2 and TR4 Recruit Multiple Epigenetic Transcriptional Corepressors That Associate Specifically with the Embryonic β-Type Globin Promoters in Differentiated Adult Erythroid Cells. Mol Cell Biol 31:3298-3311, 2011.*
GenBank Accession No. AAF01498.1, dated Oct. 8, 1999, 2 pages.
GenBank Accession No. CAA66150.1, dated Jan. 27, 1997, 2 pages.
GenBank Accession No. FJ766333, dated Mar. 17, 2009, 1 page.
GenBank Accession No. NP_001009999.1, Aug. 19, 2012, 3 pages.
GenBank Accession No. NP_001518.3, dated Aug. 5, 2012, 3 pages.
GenBank Accession No. NP_003288, dated Jun. 27, 2012, 3 pages.
GenBank Accession No. NP_003289, dated Aug. 19, 2012, 3 pages.
GenBank Accession No. NP_003874.2, dated Jul. 7, 2012, 3 pages.
GenBank Accession No. NP_004680. Dated Aug. 12, 2012, 4 pages.
GenBank Accession No. NP_004955.2, dated Aug. 19, 2012, 4 pages.
GenBank Accession No. NP_694587.3, dated Jun. 30, 2012, 2 pages.
GenBank Accession No. NP-001264, dated Jun. 26, 2012, 7 pages.
GenBank Accession No. P26358, dated Jul. 11, 2012, 30 pages.
GenBank Accession No. X52069, dated Aug. 28, 1991, 1 page.
Antoniou, 1991, "Induction of erythroid-specific expression in murine erythroleukemia (MEL) cell lines," *Methods in Molecular Biology: Gene Transfer and Expression Protocols*; Ed., Murray, 7:421-734, Humana, Clifton, NJ.
Atweh et al., "Pharmacologic induction of fetal hemoglobin production," *Hematol. Oncol. Clin. North Am.*, 2010, 24:1131-1144.
Binda et al., "Biochemical, structural, and biological evaluation of tranylcypromine derivatives as inhibitors of histone demethylases LSD1 and LSD2," *J. Am. Chem. Soc.*, 2010, 132:6827-6833.
Bradner et al., "Chemical genetic strategy identifies histone deacetylase 1 (HDAC1) and HDAC2 as therapeutic targets in sickle cell disease," *PNAS USA*, 2010, 107:12617-12622.
Cui et al., "Nuclear receptors TR2 and TR4 recruit multiple epigenetic transcriptional corepressors that associate specifically with the embryonic β-type globin promoters in differentiated adult erythroid cells," *Mol. Cell. Biol.*, 2011, 31:3298-3311.
Dayhoff et al., "A model of evolutionary change in proteins," In: *Atlas of Protein Sequence and Structure*, 1978, M.O. Dayhoff, ed., pp. 345-352. National Biomedical Research Foundation, Washington, DC.
de Boer et al., "Efficient biotinylation and single-step purification of tagged transcription factors in mammalian cells and transgenic mice," *PNAS USA*, 2003, 10:7480-7485.
Farrelly et al. "A high-throughput assay for mitochondrial membrane potential in permeabilized yeast cells," *Analytical Biochemistry*, 2001, 293:269-276.
Frietze et al., "ZNF274 Recruits the Histone Methyltransferase SETDB1 to the 3' Ends of ZNF Genes," *PLoS One*, 2010, 5:e15082.
Giarratana et al., "Ex vivo generation of fully mature human red blood cells from hematopoietic stem cells," *Nat. Biotechnol.*, 2005, 23:69-74.

(Continued)

*Primary Examiner* — Brandon Fetterolf
*Assistant Examiner* — Yih-Horng Shiao
(74) *Attorney, Agent, or Firm* — Fish & Richardson P.C.

(57) ABSTRACT

This disclosure describes methods of screening for compounds that disrupt the interaction between DNMT1 and the gamma-globin promoter or between LSD-1 and the gamma-globin promoter. This disclosure describes methods of screening for compounds that de-repress the gamma-globin gene.

12 Claims, 16 Drawing Sheets

(56) References Cited

OTHER PUBLICATIONS

Lakowski et al., "CoREST-like complexes regulate chromatin modification and neuronal gene expression," *J. Mol. Neurosci.*, 2006, 29:227-239.

Le Douarin et al., "A possible involvement of TIF1 alpha and TIF1 beta in the epigenetic control of transcription by nuclear receptors," *EMBO J.*, 1996, 15:6701-6715.

Lee et al., "An essential role for CoREST in nucleosomal histone 3 lysine 4 demethylation," *Nature*, 2005, 437:432-435, Epub Aug. 3, 2005.

Lee et al., "Histone H3 lysine 4 demethylation is a target of nonselective antidepressive medications," *Chem. Biol.*, 2006, 13:563-567.

Mabaera et al., "Neither DNA hypomethylation nor changes in the kinetics of erythroid differentiation explain 5-azacytidine's ability to induce human fetal hemoglobin," *Blood*, 2008, 111:411-420, Epub Oct. 4, 2007.

Meiler et al., "Pomalidomide augments fetal hemoglobin production without the myelosuppressive effects of hydroxyurea in transgenic sickle cell mice," *Blood*, 2011, 118:1109-1112.

Needham et al., "LCR/MEL: a versatile system for high-level expression of heterologous proteins in erythroid cells," *Nuc. Acids Res.*, 1992, 20:997-1003.

O'Geen et al., "Genome-wide binding of the orphan nuclear receptor TR4 suggests its general role in fundamental biological processes," *BMC Genomics*, 2010, 11:689.

Orkin et al., "Differentiation in erythroleukemic cells and their somatic hybrids ," *PNAS USA*, 1975, 72:98-102.

Pace and Zein, "Understanding mechanisms of gamma-globin gene regulation to develop strategies for pharmacological fetal hemoglobin induction," *Dev. Dyn.*, 2006, 235:1727-1737.

Ramirez and Hagman, "The Mi-2/NuRD complex: a critical epigenetic regulator of hematopoietic development, differentiation and cancer," *Epigenetics*, 2009, 4:532-536.

Rodriguez et al., "GATA-1 forms distinct activating and repressive complexes in erythroid cells," *EMBO J.*, 2005, 24:2354-2366.

Rodriguez et al., "Isolation of transcription factor complexes by in vivo biotinylation tagging and direct binding to streptavidin beads," *Methods Mol. Biol.*, 2006, 338:305-323.

Rybak et al., "In vivo protein biotinylation for identification of organ-specific antigens accessible from the vasculature," *Nat. Methods*, 2005, 2:291-298.

Sankaran et al., "Developmental and species-divergent globin switching are driven by BCL11A," *Nature*, 2009, 460:1093-1097, Epub Aug. 5, 2009.

Shevchenko et al., "Mass Spectrometric Sequencing of Proteins from Silver-Stained Polyacrylamide Gels," *Anal. Chem.*, 1996, 68:850-858.

Shi et al., "Histone demethylation mediated by the nuclear amine oxidase homolog LSD1," *Cell*, 2004, 119:941-953.

Slighton et al., "Human fetal G gamma- and A gamma-globin genes: complete nucleotide sequences suggest that DNA can be exchanged between these duplicated genes," *Cell*, 1980, 21:627-638.

Tanabe et al. "Embryonic and fetal β-globin gene repression by the orphan nuclear receptors, TR2 and TR4," *EMBO J.*, 2007, 26:2295-2306.

Tanabe et al., "An embryonic/fetal beta-type globin gene repressor contains a nuclear receptor TR2/TR4 heterodimer," *EMBO J.*, 2002, 21:3434-3442.

Tanimoto et al., "Context-dependent EKLF responsiveness defines the developmental specificity of the human epsilon-globin gene in erythroid cells of YAC transgenic mice," *Genes Dev.*, 2000, 14:2778-2794.

Xu et al., "Correction of sickle cell disease in adult mice by interference with fetal hemoglobin silencing," *Science*, 2011, 334:993-996.

Yang et al., "The Rpd3/Hdal family of lysine deacetylases: from bacteria to yeast to mice and men," *Nat. Rev. Mol. Cell. Biol.*, 2008, 9:206-218.

International Search Report and Written Opinion; Jan. 2, 2013; World Intellectual Property Organization (WIPO) (International Bureau of); PCT/US2012/039368; 11 pages.

Cao et al; Induction of human gamma globin gene expression by histone deacetylase inhibitors; Blood; 2004, Epub 2003; 103(2):701-709.

Langdon and Kaufman; Gamma-globin gene promoter elements required for interaction with globin enhancers; Blood; 1998; 91(1):309-318.

Tanabe et al; Embryonic and fetal beta-globin gene repression by the orphan nuclear receptors, TR2 and TR4; EMBO J; 2007; 26(9):2295-2306.

Bohacek et al., "Identification of novel small-molecule inducers of fetal hemoglobin using pharmacophore and 'PSEUDO' receptor models," Chem Biol Drug Des., 67(5):318-328, May 2006.

Boosalis et al., "Short-chain fatty acid derivatives stimulate cell proliferation and induce STAT-5 activation," Blood, 97 (10):3259-3267, May 15, 2001.

Ghoshal et al., "5-Aza-deoxycytidine induces selective degradation of DNA methyltransferase 1 by a proteasomal pathway that requires the KEN box, bromo-adjacent homology domain, and nuclear localization signal," Mol Cell Biol., 25(11):4727-4741, Jun. 2005.

Kolodziej et al., "Characterization of nuclear orphan receptor TR2/TR4 complexes in erythroid cells," Blood Cells, Molecules, and Diseases, 38(2):149, Feb. 2, 2007.

Perrine, "Fetal globin induction—can it cure beta thalassemia?" Hematology Am Soc Hematol Educ Program., 2005:38-44, 2005.

Steinberg et al., "Pharmacologic modulation of fetal hemoglobin," Medicine, 80(5):328-344, Sep. 1, 2001.

Szulawska et al., "Accumulation of gamma-globin mRNA and induction of irreversible erythroid differentiation after treatment of CML cell line K562 with new doxorubicin derivatives," Biochem Pharmacol., 73(2):175-184. Epub Oct. 4, 2006.

Yokochi and Robertson, "Doxorubicin inhibits DNMT1, resulting in conditional apoptosis," Mol Pharmacol., 66 (6):1415-1420. Epub Aug. 31, 2004.

European Search Report for Application No. 12789967, dated Dec. 1, 2014, 9 pages.

* cited by examiner

SEQUENCE LISTING

<160> NUMBER OF SEQ ID NOS: 22

<210> SEQ ID NO 1
<211> LENGTH: 29
<212> TYPE: DNA

```
<213> ORGANISM: Artificial Sequence
<220> FEATURE:
<223> OTHER INFORMATION: oligonucleotide

<400> SEQUENCE: 1
gaaagaatac ctccatatct aatgtgcat                                    29

<210> SEQ ID NO 2
<211> LENGTH: 26
<212> TYPE: DNA
<213> ORGANISM: Artificial Sequence
<220> FEATURE:
<223> OTHER INFORMATION: oligonucleotide

<400> SEQUENCE: 2
ctgcattatt ctttgaagct attggt                                       26

<210> SEQ ID NO 3
<211> LENGTH: 18
<212> TYPE: DNA
<213> ORGANISM: Artificial Sequence
<220> FEATURE:
<223> OTHER INFORMATION: oligonucleotide

<400> SEQUENCE: 3
ggaccccacc cctgtctt                                                18

<210> SEQ ID NO 4
<211> LENGTH: 20
<212> TYPE: DNA
<213> ORGANISM: Artificial Sequence
<220> FEATURE:
<223> OTHER INFORMATION: oligonucleotide

<400> SEQUENCE: 4
ttacccctcc ccaggactct                                              20

<210> SEQ ID NO 5
<211> LENGTH: 20
<212> TYPE: DNA
<213> ORGANISM: Artificial Sequence
<220> FEATURE:
<223> OTHER INFORMATION: oligonucleotide

<400> SEQUENCE: 5
gaagcctgat tccgtagagc                                              20

<210> SEQ ID NO 6
<211> LENGTH: 27
<212> TYPE: DNA
<213> ORGANISM: Artificial Sequence
<220> FEATURE:
<223> OTHER INFORMATION: oligonucleotide

<400> SEQUENCE: 6
caactgatcc tacctcacct tatatgc                                      27

<210> SEQ ID NO 7
<211> LENGTH: 20
<212> TYPE: DNA
<213> ORGANISM: Artificial Sequence
<220> FEATURE:
<223> OTHER INFORMATION: oligonucleotide

<400> SEQUENCE: 7
cgggatgggc attaaaggta                                              20
```

<210> SEQ ID NO 8
<211> LENGTH: 24
<212> TYPE: DNA
<213> ORGANISM: Artificial Sequence
<220> FEATURE:
<223> OTHER INFORMATION: oligonucleotide

<400> SEQUENCE: 8
aacaacctgt gtcagaagca gatg                24

<210> SEQ ID NO 9
<211> LENGTH: 16
<212> TYPE: DNA
<213> ORGANISM: Artificial Sequence
<220> FEATURE:
<223> OTHER INFORMATION: oligonucleotide

<400> SEQUENCE: 9
cgcggtccgg tgtttg                16

<210> SEQ ID NO 10
<211> LENGTH: 25
<212> TYPE: DNA
<213> ORGANISM: Artificial Sequence
<220> FEATURE:
<223> OTHER INFORMATION: oligonucleotide

<400> SEQUENCE: 10
ggaaaggtag gagttgagag gtgaa                25

<210> SEQ ID NO 11
<211> LENGTH: 24
<212> TYPE: DNA
<213> ORGANISM: Artificial Sequence
<220> FEATURE:
<223> OTHER INFORMATION: oligonucleotide

<400> SEQUENCE: 11
tcccactctg tgggttgtct gttt                24

<210> SEQ ID NO 12
<211> LENGTH: 27
<212> TYPE: DNA
<213> ORGANISM: Artificial Sequence
<220> FEATURE:
<223> OTHER INFORMATION: oligonucleotide

<400> SEQUENCE: 12
cccttctaca cattggctta ggaaagg                27

<210> SEQ ID NO 13
<211> LENGTH: 22
<212> TYPE: DNA
<213> ORGANISM: Artificial Sequence
<220> FEATURE:
<223> OTHER INFORMATION: oligonucleotide

<400> SEQUENCE: 13
gatgccataa agcacctgga tg                22

<210> SEQ ID NO 14
<211> LENGTH: 24
<212> TYPE: DNA
<213> ORGANISM: Artificial Sequence
<220> FEATURE:

```
<223> OTHER INFORMATION: oligonucleotide

<400> SEQUENCE: 14
ttgcagaata aagcctatcc ttga                                              24

<210> SEQ ID NO 15
<211> LENGTH: 24
<212> TYPE: DNA
<213> ORGANISM: Artificial Sequence
<220> FEATURE:
<223> OTHER INFORMATION: oligonucleotide

<400> SEQUENCE: 15
aactgtgttc actagcaacc tcaa                                              24

<210> SEQ ID NO 16
<211> LENGTH: 22
<212> TYPE: DNA
<213> ORGANISM: Artificial Sequence
<220> FEATURE:
<223> OTHER INFORMATION: oligonucleotide

<400> SEQUENCE: 16
gagtggacag atccccaaag ga                                                22

<210> SEQ ID NO 17
<211> LENGTH: 20
<212> TYPE: DNA
<213> ORGANISM: Artificial Sequence
<220> FEATURE:
<223> OTHER INFORMATION: oligonucleotide

<400> SEQUENCE: 17
tggccattct caaagggatt                                                   20

<210> SEQ ID NO 18
<211> LENGTH: 18
<212> TYPE: DNA
<213> ORGANISM: Artificial Sequence
<220> FEATURE:
<223> OTHER INFORMATION: oligonucleotide

<400> SEQUENCE: 18
cagcacgcca acgagaca                                                     18

<210> SEQ ID NO 19
<211> LENGTH: 18
<212> TYPE: DNA
<213> ORGANISM: Artificial Sequence
<220> FEATURE:
<223> OTHER INFORMATION: oligonucleotide

<400> SEQUENCE: 19
cccggtgcct tgtctgct                                                     18

<210> SEQ ID NO 20
<211> LENGTH: 18
<212> TYPE: DNA
<213> ORGANISM: Artificial Sequence
<220> FEATURE:
<223> OTHER INFORMATION: oligonucleotide

<400> SEQUENCE: 20
gtgaaatcgg cagggtgg                                                     18
```

```
<210> SEQ ID NO 21
<211> LENGTH: 21
<212> TYPE: DNA
<213> ORGANISM: Artificial Sequence
<220> FEATURE:
<223> OTHER INFORMATION: oligonucleotide

<400> SEQUENCE: 21
accgcagcta ggaataatgg a                                               21

<210> SEQ ID NO 22
<211> LENGTH: 19
<212> TYPE: DNA
<213> ORGANISM: Artificial Sequence
<220> FEATURE:
<223> OTHER INFORMATION: oligonucleotide

<400> SEQUENCE: 22
gcctcagttc cgaaaacca                                                  19
```

EPIGENETIC CO-REPRESSORS OF THE GAMMA-GLOBIN GENE AND METHODS OF USING SAME

CROSS-REFERENCE TO RELATED APPLICATIONS

This application claims the benefit of priority under 35 U.S.C. §119(e) to U.S. Applications No. 61/588,245 filed on Jan. 19, 2012, and U.S. Application No. 61/490,175 filed on May 26, 2011, both of which are incorporated herein by reference in their entirety.

FEDERALLY SPONSORED RESEARCH OR DEVELOPMENT

This invention was made with government support under Grant Nos. DK086956 and HL024415 awarded by the National Institutes of Health. The government has certain rights in the invention.

TECHNICAL FIELD

This disclosure generally relates to the globin genes, specifically the gamma-globin gene.

BACKGROUND

Regulatory pathways that control development through temporally specified gene activation and repression mechanisms have been recognized as "epigenetic" (i.e. heritable changes not involving alterations in the primary DNA code). The beta-globin locus is a paradigm for epigenetic regulation of lineage- and developmentally-specific gene expression. The human beta-globin locus is composed of epsilon- (embryonic), G-gamma- and A-gamma-(fetal) and delta- and beta- (adult) globin genes, which are spatially arranged from 5' to 3' and developmentally expressed in the same order. A number of polypeptides involved in the epigenetic regulation of the beta-globin locus and their uses are described herein.

SUMMARY

In one aspect, a method of screening for compounds that stimulate expression of a gamma-globin gene in a definitive erythroid cell is provided. Such a method typically includes contacting a recombinant cell with a test compound, wherein the recombinant cell comprises a nucleic acid sequence encoding a DNA methyltransferase I (DNMT1) polypeptide and a nucleic acid sequence encoding a detectable polypeptide operably linked to a human gamma-globin gene promoter; and measuring the amount of the detectable polypeptide in the presence and absence of the test compound. Generally, an increase in the amount of the detectable polypeptide in the presence of the test compound compared to the amount of the detectable polypeptide in the absence of the test compound identifies a test compound as a compound that stimulates expression of a gamma-globin gene in a definitive erythroid cell.

In another aspect, a method of screening for compounds that stimulate expression of a gamma-globin gene in a definitive erythroid cell is provided. Such a method typically includes contacting a recombinant cell with a test compound, wherein the recombinant cell comprises a nucleic acid sequence encoding the lysine-specific histone demethylase (LSD)-1 polypeptide and a nucleic acid sequence encoding a detectable polypeptide operably linked to a human gamma-globin gene promoter; and measuring the amount of the detectable polypeptide in the presence and absence of the test compound. Generally, an increase in the amount of the detectable polypeptide in the presence of the test compound compared to the amount of the detectable polypeptide in the absence of the test compound identifies a test compound as a compound that stimulates expression of a gamma-globin gene in a definitive erythroid cell.

In still another aspect, a method of screening for compounds that de-repress the human gamma-globin gene in a definitive erythroid cell is provided. Typically, such a method includes contacting a recombinant cell with a test compound, wherein the recombinant cell comprises a nucleic acid sequence encoding a TR2 polypeptide, a nucleic acid sequence encoding a TR4 polypeptide, a nucleic acid sequence encoding a DNMT1 polypeptide or a LSD-1 polypeptide or both, and a nucleic acid sequence encoding a detectable polypeptide operably linked to a human beta-globin gene promoter, and optionally, one or more nucleic acids encoding a nucleosome remodeling and deacetylase (NuRD) complex, a CoREST complex, an HDAC3 polypeptide, and a transcriptional intermediary factor (TIF)-1beta polypeptide; and measuring the amount of the detectable polypeptide in the presence and absence of the test compound. Generally, an increase in the amount of the detectable polypeptide in the presence of the test compound compared to the amount of the detectable polypeptide in the absence of the test compound identifies a test compound as a compound that de-represses the human gamma-globin gene in a definitive erythroid cell.

Representative compounds include small molecules, polypeptides, synthetic compounds, naturally-occurring compounds, antibodies, antigen-binding fragment, and antigens. In some embodiments, at least one of the nucleic acid sequences from each method is heterologous to the recombinant cell. In some embodiments, the detectable polypeptide is luciferase, GUS, beta-gal, or CAT.

In another aspect, a method of treating a beta-globin disorder in an individual in need of such treatment is provided. Such methods typically include administering an effective amount of a compound that inhibits LSD-1 to an individual suffering from a beta-globin disorder. Generally, the effective amount of the compound that inhibits LSD-1 is an amount that de-represses the human gamma-globin gene, thereby treating the beta-globin disorder. Representative compounds that inhibit LSD-1 include tranylcypromine, derivatives of tranylcypromine, analogues of tranylcypromine, polyamine analogues, and a 2-PCPA derivative. In some embodiments, the beta-globin disorder is selected from the group consisting of sickle cell disease and beta-thalassemia.

In another aspect, a method of treating a beta-globin disorder in an individual in need of such treatment is provided. Such methods typically include administering an effective amount of a compound that inhibits DNMT1 to an individual suffering from a beta-globin disorder. Generally, the effective amount of the compound that inhibits DNMT1 is an amount that de-represses the human gamma-globin gene, thereby treating the beta-globin disorder. Representative compounds that inhibit DNMT1 include doxorubicin, SGI-110, SGI-1036, disulfuram, azacytidine, and decitabine. In some embodiments, the beta-globin disorder is selected from the group consisting of sickle cell disease and beta-thalassemia.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

Part A

Part B

Figure 11:
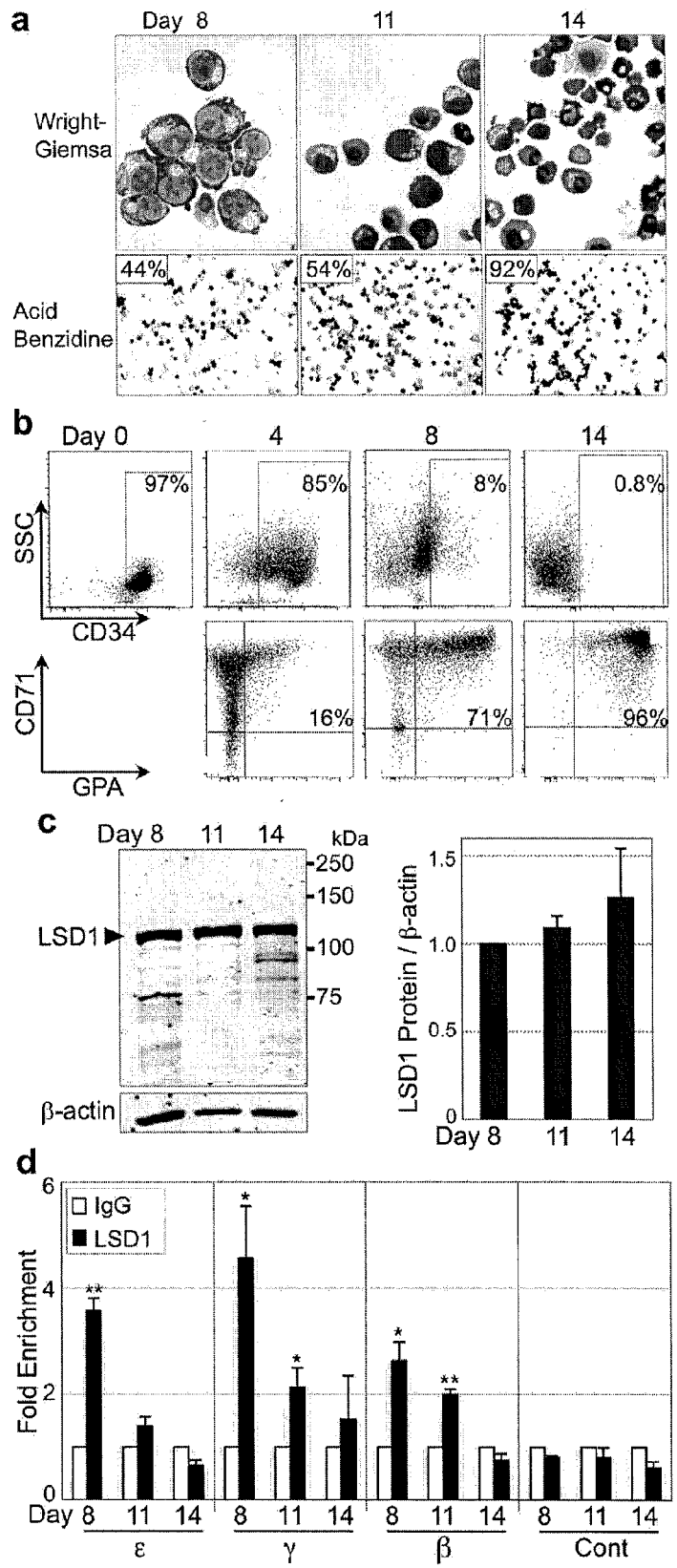

FIG. 11 shows the association of LSD1 with beta-like globin gene promoters in primary human erythroid cells. Panel (a) demonstrates erythroid differentiation of human CD34+ hematopoietic progenitor cells confirmed by morphology and hemoglobin accumulation examined by Wright-Giemsa and acid benzidine staining, respectively, on day 8, 11 and 14 of the differentiation culture. Numbers indicate percentages of cells stained by the acid benzidine method (averages of three biological replicates). Panel (b) is the flow-cytometric analysis of differentiating erythroid cells. Shown are dot plots of CD34 expression and side scatter (SSC) intensity (upper row) with percentages of cells expressing CD34, and dot plots of transferrin receptor (CD71) and glycophorin A (GPA) expression (lower row) with percentages of cells double-positive for both CD71 and GPA. The percentages are averages of two to four biological replicates. Panel (c) is a Western blot showing LSD1 expression along with β-actin as a loading control. The bar graph shows relative abundance of LSD1, normalized to β-actin, on day 8. Panel (d) is the results of ChIP assay showing LSD1 binding at the human embryonic epsilon-, fetal gamma- and adult beta-globin gene promoters. Presented is relative abundance of DNA precipitated with the anti-LSD1 antibody, normalized to control IgG. As a negative control (Cont), an intergenic region between the epsilon- and Ggamm-globin genes was used. Statistical significance of LSD1 enrichment at the promoters as compared to control IgG values is indicated with asterisks.

Figure 12:
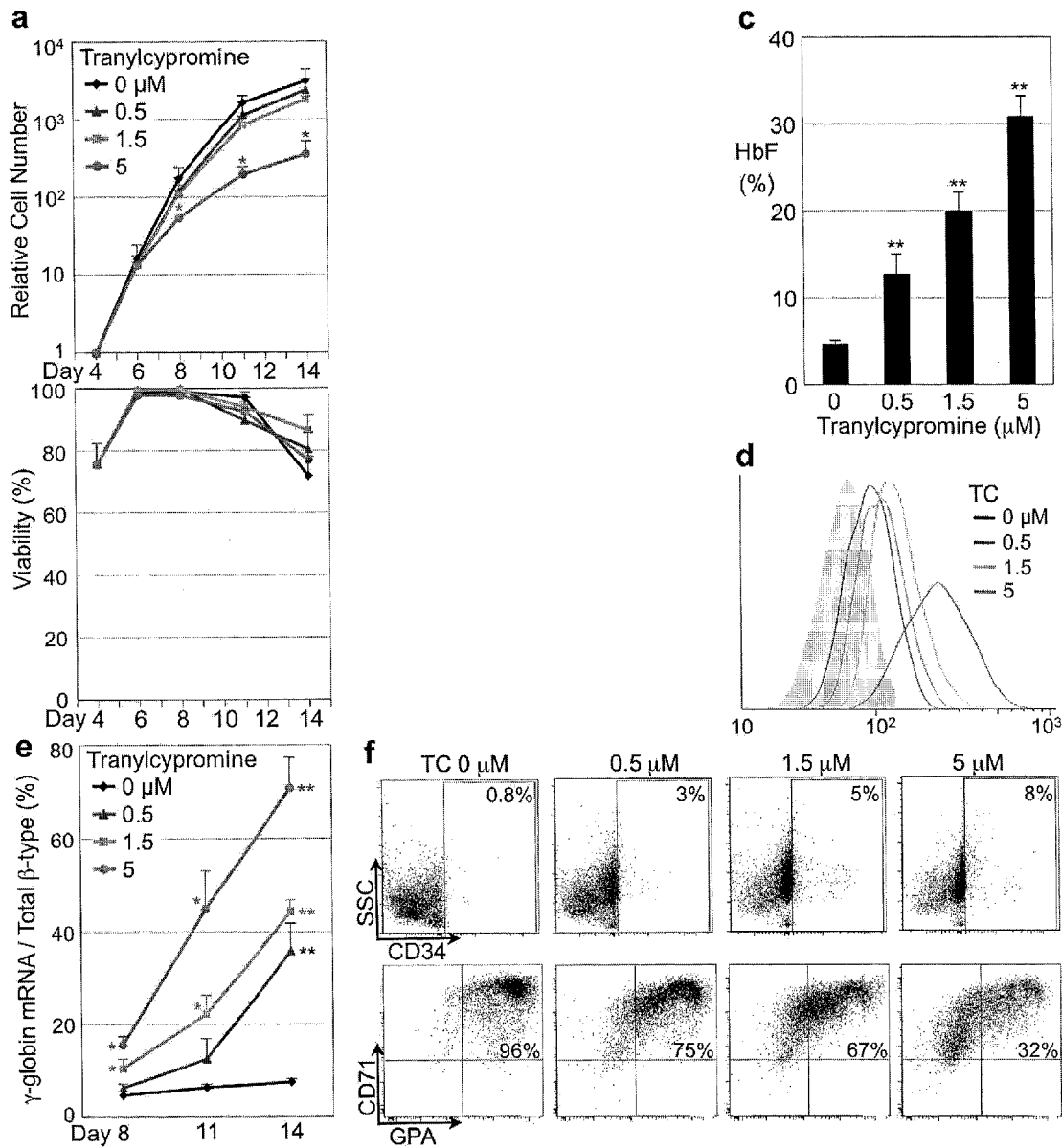

FIG. 12 shows the induction of fetal gamma-globin synthesis by LSD1 inhibitor tranylcypromine. Panel (a) shows the proliferation (upper graph) and viability (lower graph) of differentiating erythroid cells exposed to tranylcypromine (TC) at indicated concentrations. Averages of three biological replicates are presented. Panel (b) shows representative HPLC chromatograms demonstrating enhanced fetal hemoglobin (HbF) synthesis (shaded area) by TC on day 14 of the culture. Numbers indicate fractional percentages of HbF and adult hemoglobin (HbA). Panel (c) is a graph demonstrating the HbF abundance determined by HPLC on day 14 as fractional percentages of total hemoglobin in TC-treated cells. Panel (d) is a flow-cytometric analysis showing induction of HbF synthesis by TC on day 14. The shaded area indicates staining with control IgG. Panel (e) is a graph showing the induction of fetal gamma-globin mRNA by TC. Relative gamma-globin mRNA abundance normalized to total beta-type globin mRNAs (sum of fetal gamma- and adult beta-globin) was determined by RT-qPCR. Averages of three biological replicates are presented. Panel (f) is a flow-cytometric analysis showing effects of TC on erythroid surface marker expression. Expression of CD34 (upper row), as well as CD71 and GPA (lower row), are shown. Percentages are averages of three or four biological replicates. Asterisks indicate statistically significant difference between untreated and TC-treated cells.

Figure 13:
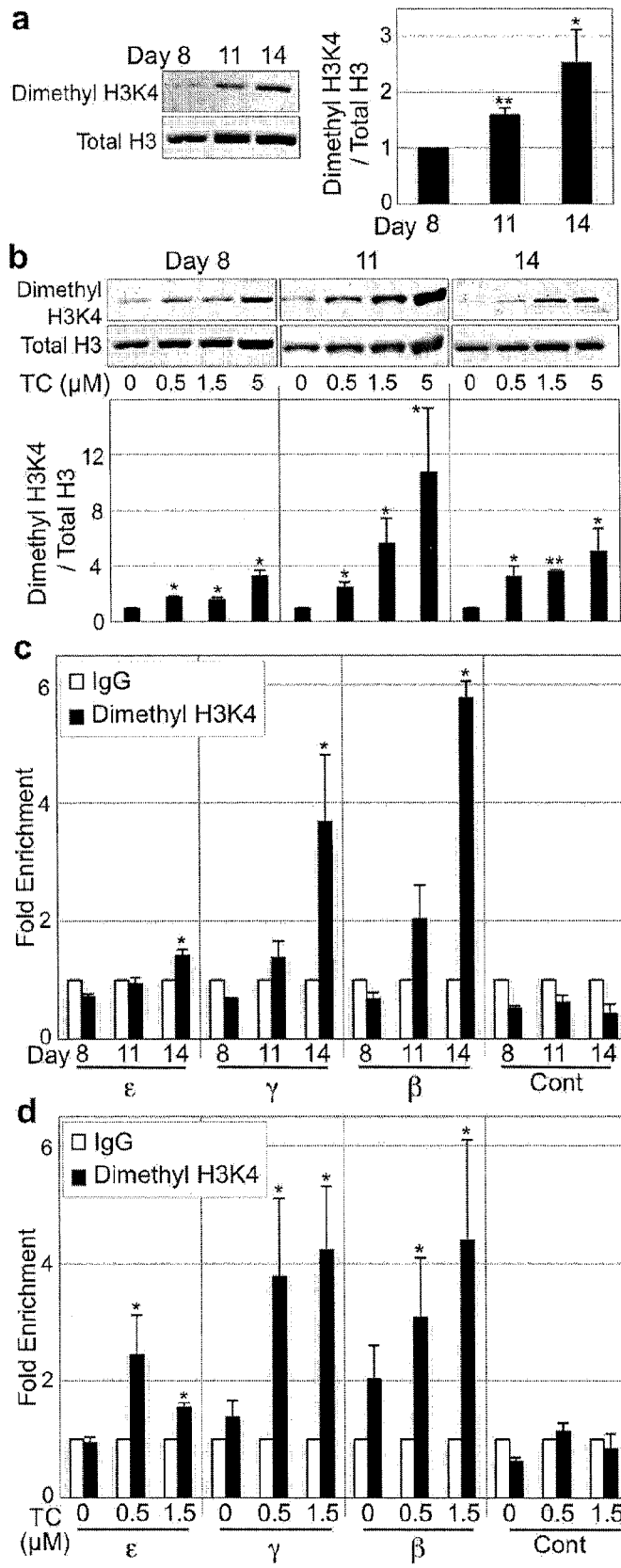

FIG. 13 shows enhanced histone H3 lysine 4 dimethylation by tranylcypromine in differentiating erythroid cells. Panel (a) shows that global histone H3 lysine 4 (H3K4) dimethylation was determined by Western blotting analysis of total cell extracts with an antibody against total histone H3 or dimethyl H3K4. The bar graph shows abundance of dimethyl-H3K4, normalized to total histone H3, and to day 8. Panel (b) shows the effects of tranylcypromine (TC) on global H3K4 dimethylation. Bar graphs demonstrate the extent of H3K4 dimethylation, normalized to untreated cells. Panel (c) shows results from ChIP assays demonstrating H3K4 dimethylation at the beta-type globin promoters during differentiation. Presented is relative abundance of DNA precipitated with the anit-dim-ethyl-H3K4 antibody, normalized to control IgG. The same negative control region (Cont) as in FIG. 11(d) was used. Panel (d) shows the results of ChIP assays demonstrating enhanced H3K4 dimethylation at the beta-type globin promoters by TC on day 11. Asterisks indicate statistically significant difference from day 8 (Panel (a)), between untreated and TC-treated cells (Panel (b)), or between anti-dimethyl-H3K4 and control antibodies (Panels (c) and (d)).

Figure 14:
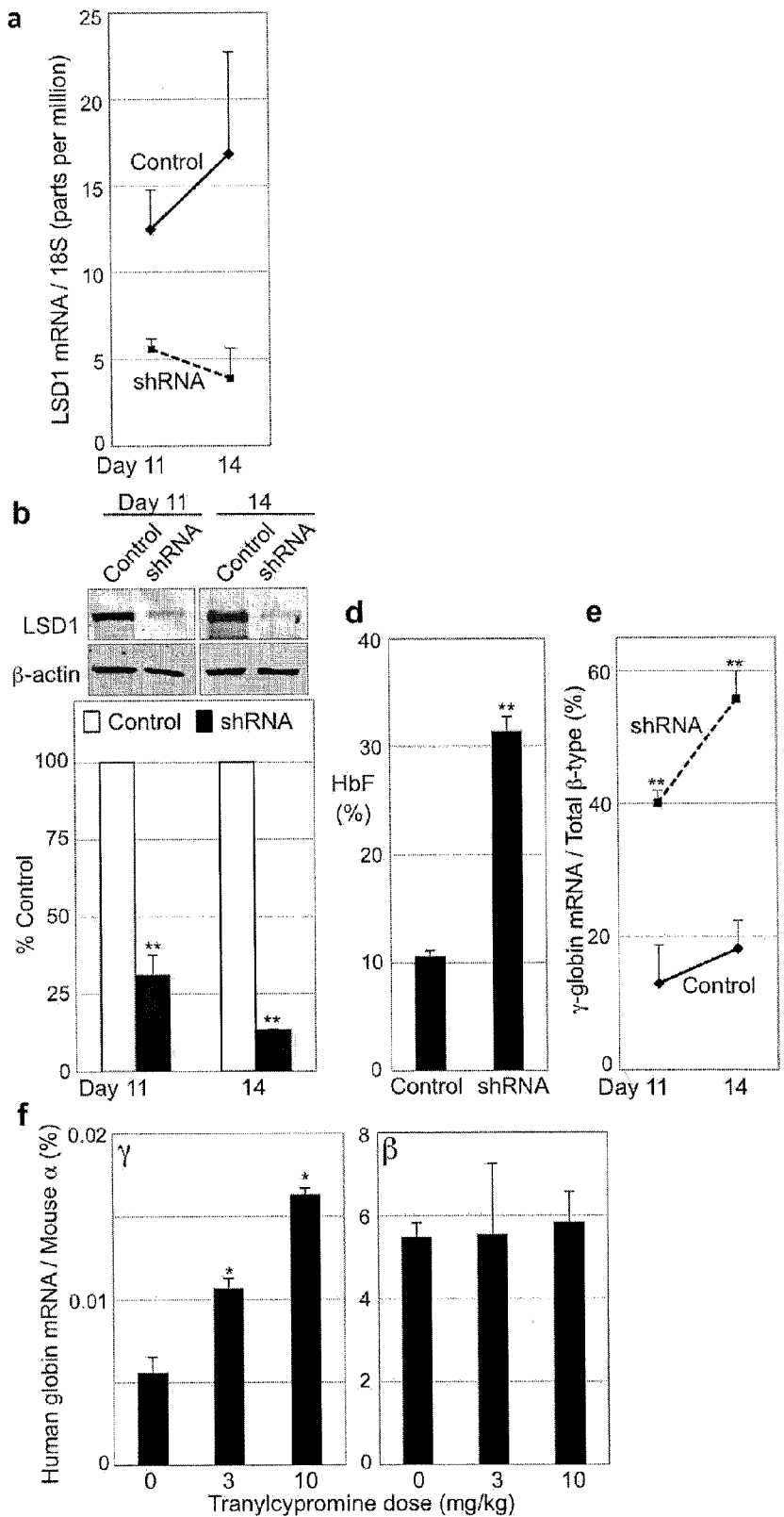

FIG. 14 shows fetal gamma-globin gene induction by LSD1 knockdown in human erythroid progenitor cells, and by tranylcypromine in mouse. Panel (a) shows LSD1 mRNA abundance in differentiating human erythroid cells infected with a lentivirus expressing a short-hairpin RNA (shRNA) against LSD1, or a control virus. Primary human erythroid cells were infected on day 4, and then selected with puromycin. Averages of three biological replicates are presented. Panel (b) is a Western blot showing abundance of LSD1 and beta-actin as an internal control in the shRNA or control virus-infected cells. The bar graph shows relative abundance of LSD1, normalized to beta-actin, and to the control cells. Panel (c) shows representative HPLC chromatograms to demonstrate enhanced fetal hemoglobin (HbF) synthesis (shaded area) by the shRNA against LSD1 on day 14 of the culture. Numbers indicate fractional percentages of HbF and HbA. Panel (d) shows HbF abundance determined by HPLC as fractional percentages of total hemoglobin in the shRNA or control virus-infected cells on day 14. Panel (e) shows the induction of fetal gamma-globin mRNA by the shRNA against LSD1. Relative gamma-globin mRNA abundance normalized to total beta-type globin mRNAs (sum of fetal gamma- and adult beta-globin) is shown. Averages of three biological replicates are presented. Panel (f) shows induction of gamma-globin gene expression by TC in transgenic mice harboring a yeast artificial chromosome containing a whole human beta-type globin locus. TC at a dose of 3 or 10 mg/kg body weight per day, or saline for control mice, was administered by subcutaneous injection, 5 days a week for 4 weeks. Fetal gamma- and adult beta-globin mRNA abundance in bone marrow cells, normalized to mouse endogenous alpha-globin, is shown. Asterisks indicate statistically significant difference between the cells infected with the shRNA and control viruses (Panels (b), (d), and (e)), or between mice administered with TC and saline (Panel (f)).

Like reference symbols in the various drawings indicate like elements.

DETAILED DESCRIPTION

Nuclear receptors, TR2 and TR4, have been shown to bind to direct repeat elements in vitro in the mouse and human embryonic and fetal beta-type globin gene promoters, and to play critical roles in the silencing of these genes. This disclosure describes additional polypeptides or complexes (e.g., DNMT1, NuRD and LSD1/CoREST repressor complexes, and HDAC3 and TIF1beta polypeptides) that co-repress the embryonic beta-type globin promoters. Interestingly, in undifferentiated murine adult erythroid cells, these co-repressors associate with both the embryonic and adult beta-type globin promoters, but, upon terminal differentiation, they specifically dissociate only from the adult beta-globin promoter, concomitant with its activation, but remain bound to the silenced embryonic globin gene promoters.

Sickle cell disease is caused by a missense mutation in the adult beta-globin gene and affects millions of people worldwide. Hemoglobin that incorporates the mutant beta-globin polypeptide polymerizes, when deoxygenated, and causes erythrocytes to acquire a stiff, sickle shape. Sickle erythrocytes are subject to premature destruction, and prone to occlude blood flow, causing vascular damage in multiple organ systems. Therapeutic agents that increase gamma-globin production are widely expected to benefit sickle cells disease patients since biochemical evidence demonstrates that gamma-globin inhibits polymerization of deoxygenized sickle hemoglobin in vitro.

Screening for Compounds that Stimulate (or De-repress) the Globin Genes

Based on the experimental results described herein, methods of screening for compounds that stimulate (or de-repress) the gamma-globin gene in adult cells are provided. For example, methods are described in which compounds are screened for those that disrupt the interaction between DNA methyltransferase 1 (DNMT1) and the gamma-globin promoter in a definitive erythroid cell, as are methods in which compounds are screened for those that disrupt the interaction between lysine-specific histone demethylase (LSD)-1 and the gamma-globin promoter in a definitive erythroid cell. Methods also are described in which compounds are screened to identify those that de-repress the human gamma-globin gene in a definitive erythroid cell (e.g., in the presence of TR2/TR4 polypeptides and/or DNMT1 polypeptide and/or a LSD-1 polypeptide).

The screening methods disclosed herein typically include contacting a recombinant cell with a test compound. For use in the screening methods herein, a recombinant cell includes nucleic acids encoding the polypeptides necessary to evaluate the interaction between the gamma-globin promoter and one or more of the co-repressors identified herein (e.g., DNMT1 or LSD-1, and, optionally, a nucleosome remodeling and deacetylase (NuRD) complex, a CoREST complex, an HDAC3 polypeptide, and a transcriptional intermediary factor (TIF)-1beta polypeptide). In addition to nucleic acids encoding one or more of the co-repressors identified herein, a nucleic acid sequence encoding a detectable polypeptide operably linked to a gamma-globin gene promoter (e.g., a human gamma-globin gene promoter) is required. It would be understood by those skilled in the art that the nucleic acids encoding the particular polypeptides can be endogenous to the cell or exogenous (e.g., heterologous) to the cell, but at least one nucleic acid is required to be exogenous for the cell to be recombinant.

The screening methods disclosed herein include measuring the amount of the detectable polypeptide in the presence and absence of the test compound. An increase in the amount of the detectable polypeptide in the presence of the test compound compared to the amount of the detectable polypeptide in the absence of the test compound identifies a test compound as a compound that disrupts the interaction between the one or more co-repressor polypeptides and the gamma-globin promoter in a definitive erythroid cell and, thereby, de-represses the gamma-globin gene.

Many of the methods described herein are highly amenable to automation and high throughput. See, for example, WO 84/03564 for a description of high throughput screening of compounds, and Farrelly et al. (2001, *Analytical Biochemistry*, 293:269-276) for a description of high throughput methods to screen for compounds that affect protein binding and transcriptional activation via protein binding.

Polypeptides, Nucleic Acids Encoding the Polypeptides, and Recombinant Cells

The novel interactions disclosed herein that ultimately result in repression of the human gamma-globin gene occur between polypeptides that are known in the art and have been described in the literature.

For example, TR2 polypeptides and TR4 polypeptides are nuclear receptors (in standard nomenclature, NR2C1 and NR2C2, respectively) that have been shown to be associated with the DRED repressor complex. The DRED repressor complex has been shown to bind to direct repeat (DR) elements found in the promoters of the epsilon- and gamma-globin genes. See, for example, US 2008/0008651 and Tanabe et al. (2007, *EMBO J.*, 26:2295-306). The amino acid sequence of a human TR2 polypeptide can be found, for example, at GenBank Accession No. NP 003288, and the amino acid sequence of a human TR4 polypeptide can be found, for example, at GenBank Accession No. NP 003289.

The DNTM 1 polypeptide is often referred to as a maintenance methyltransferase, rather than a de novo enzyme, but it has been shown that the specific activity of DNTM1 on unmethylated DNA is greater than the de novo DNA methyltransferases, DNMT3A and DNMT3B. The present disclosure is the first to demonstrate a physical link between a nuclear receptor and DNMT1, indicating that DNMT1 may play a role in developmental gene silencing triggered by nuclear receptors. The amino acid sequence of a human DNTM1 polypeptide can be found, for example, at GenBank Accession No. P26358.

The LSD-1 polypeptide (see, for example, Shi et al., 2004, *Cell*, 119:941-53) often associates with the CoREST complex, which contains both HDAC1/2 and H3K4 demethylase. Recently, it was shown that LSD-1 also can act as a transcriptional co-activator for the androgen receptor by stimulating demethylation of histone H3K9, a repressive histone mark, and it was subsequently shown that LSD-1 also is required for ER-regulated transcriptional activation. The amino acid sequence of LSD-1 can be found, for example, at GenBank Accession No. NP_001009999.1 (LSD-1A) and NP_694587.3 (LSD-1B).

In addition to the primary components of the silencing complex, which, in addition to the TR2/TR4 heterodimer, includes DNTM-1 and/or LSD-1, several other polypeptides were identified that may be involved, with one or more of the primary components, in the repression of the adult human gamma-globin gene. For example, the NuRD complex, the CoREST complex, HDAC3 and TIF1beta also may be involved in repression of the adult human gamma-globin promoter.

The NuRD complex is the only known multi-protein complex containing both histone deacetylase (HDAC1/2) and chromatin remodeling ATPase (Mi2) polypeptides, as well as a number of others. NuRD has been shown to interact with a number of transcription factors, and analyses of mice bearing targeted mutations of NuRD subunits have revealed their important roles in various aspects of development, including a role for Mi2beta in self-renewal and multilineage differentiation of hematopoietic stem cells. MTA1, the signature subunit of NuRD, was previously shown to directly interact with the estrogen receptor (ER) and to act as a co-repressor of ER-mediated transcriptional repression. For a review of the NuRD complex, see, for example, Ramirez et al., 2009, *Epigenetics*, 4:532-6 and Yang et al., 2008, *Nat. Rev. Mol. Cell. Biol.*, 9:206-18. Representative amino acid sequences of polypeptides involved in the NuRD repressor complex include, for example, GenBank Accession Nos. NP_004955.2 (HDAC1), NP_001518.3 (HDAC2), NP-001264 (Mi2beta), and NP_004680 (MTA1).

As indicated herein, the CoREST complex typically includes a CoREST protein, HDAC1/2, H3K4 demethylase and LSD-1. The CoREST complex has been reported to be a histone deacetylase complex. A review of the CoREST complex can be found, for example, in Lakowski et al., 2006, *J. Mol. Neurosci.*, 29:227-39. Representative amino acid sequences of HDAC1/2 are indicated above, and a representative amino acid sequence of CoREST can be found, for example, at GenBank Accession No. AAF01498.1. See, also, Lee et al., 2005, *Nature*, 437:432-5.

HDAC3 is known to be a component of the N-CoR/SMRT complex, which was originally identified as a co-repressor for the thyroid hormone and retinoic acid receptors. Since an interaction between TR2/TR4 and N-CoR/SMRT was not detected in the experiments described herein, HDAC3 may bind directly to TR2/TR4 in erythroid cells without the other components of the N-CoR/SMRT complex. A representative amino acid sequence of a human HDAC3 polypeptide can be found, for example, at GenBank Accession No. NP_003874.2.

TIF1beta (see, for example, Le Douarin et al., 1996, *EMBO J.*, 15:6701-15), also known as KAP-1 (KRAB domain-associated protein), has been proposed to act as the universal transcriptional co-repressor for the KRAB (Krüppel-associated box) domain-containing zinc finger transcription factors. In mediating transcriptional repression, TIF1beta is thought to recruit the NuRD complex to a KRAB protein. TIF1beta also interacts directly with HP1 (heterochromatin protein 1) proteins, further implicating its role in epigenetic transcriptional repression, in this case through heterochromatin formation. A representative amino acid sequence of a human TIF1beta polypeptide can be found, for example, at GenBank Accession No. CAA66150.1.

Detectable polypeptides are used routinely in the art, and simply refer to any polypeptide that can be detected, either directly or indirectly. Detectable polypeptides are sometimes referred to as reporter proteins. Without limitation, representative detectable polypeptides include luciferase (e.g., U.S. Pat. Nos. 7,871,803; and 7,939,649), fluorescent proteins (e.g., U.S. Pat. Nos. 7,892,791; 7,897,385; and 7,910,714), beta-galactosidase, beta-glucuronidase (GUS), and chloramphenyl acetyltransferase (CAT). It would be understood that any number of other proteins can be used as a "detectable polypeptide" using, for example, an antibody specific for that protein. For example, in certain instances, the gamma-globin protein can be used as the "detectable polypeptide" to evaluate the effect that a compound has on the various co-repressors identified herein.

The detectable polypeptide is operably linked to a gamma-globin promoter. The gamma-globin gene is typically transcriptionally active in a fetus, but is then silenced in the adult organisms. See, for example, Pace et al., 2006, Dev. Dyn., 235:1727-37. Representative nucleic acid sequences of a human gamma-globin promoter can be found, for example, at GenBank Accession No. FJ766333 or X52069. See, also, Slighton et al., 1980, *Cell*, 21:627-38.

With respect to polypeptides, the term "purified" refers to a polypeptide that has been separated or purified from cellular components that naturally accompany it. Typically, the polypeptide is considered "purified" when it is at least 70% (e.g., at least 75%, 80%, 85%, 90%, 95%, or 99%) by dry weight, free from the proteins and naturally occurring molecules with which it is naturally associated. Since a polypeptide that is chemically synthesized is, by nature, separated from the components that naturally accompany it, a synthetic polypeptide is "purified".

Polypeptides can be purified from natural sources (e.g., cell lysates) by known methods such as DEAE ion exchange, gel filtration, and hydroxyapatite chromatography. In addition, a purified polypeptide can be obtained by chemical synthesis. The extent of purity of a polypeptide can be measured using any appropriate method, e.g., column chromatography, polyacrylamide gel electrophoresis, or HPLC analysis. As described in more detail below, a purified polypeptide also can be obtained by expressing a nucleic acid encoding the polypeptide.

The above-described polypeptides can be encoded by the respective nucleic acid sequences associated with the above-referenced GenBank Accession Numbers. Those of skill in the art would understand, however, that, based on the degenerate code, a number of different nucleic acids can be designed that encode the same polypeptide. The term "nucleic acid" can refer to DNA molecules and RNA molecules as well as analogs of the DNA or RNA molecule generated using nucleotide analogs. A nucleic acid as described herein can be single-stranded or double-stranded, which generally is dependent upon its intended use.

As used herein, an "isolated" nucleic acid is a nucleic acid that is separated from other nucleic acids that are usually associated with the isolated nucleic acid. Thus, an "isolated" nucleic acid includes, without limitation, a nucleic acid that is free of sequences that naturally flank one or both ends of the nucleic acid in the genome of the organism from which the isolated nucleic acid is derived (e.g., a cDNA or genomic DNA fragment produced by PCR or restriction endonuclease digestion). In addition, an isolated nucleic acid molecule can include an engineered nucleic acid such as a recombinant or a synthetic nucleic acid. A nucleic acid existing among hundreds to millions of other nucleic acid molecules within, for example, a nucleic acid library (e.g., a cDNA, or genomic library) or a portion of a gel (e.g., agarose, or polyacrylamide) containing restriction-digested genomic DNA is not to be considered an isolated nucleic acid.

Isolated nucleic acids can be obtained using techniques routine in the art. For example, isolated nucleic acids can be obtained using any method including, without limitation, recombinant nucleic acid technology, and/or the polymerase chain reaction (PCR). General PCR techniques are described, for example in *PCR Primer: A Laboratory Manual*, 1995, Dieffenbach & Dveksler, Eds., Cold Spring Harbor Laboratory Press. Recombinant nucleic acid techniques include, for example, restriction enzyme digestion and ligation, which can be used to isolate a nucleic acid. Isolated nucleic acids also can be chemically synthesized, either as a single nucleic acid or as a series of oligonucleotides.

In addition to naturally-occurring sequences, the skilled artisan will further appreciate that changes can be introduced into a nucleic acid using methods routine in the art, thereby leading to changes in the amino acid sequence of the encoded polypeptide. For example, changes can be introduced into nucleic acid coding sequences leading to conservative amino acid substitutions at one or more amino acid residues. A "conservative amino acid substitution" is one in which one amino acid residue is replaced with a different amino acid residue having similar characteristics (see, for example, Dayhoff et al., 1978, in *Atlas of Protein Sequence and Structure*, 5(3):345-352).

A nucleic acid or polypeptide sequence can be compared to another sequence and described in terms of its percent sequence identity. In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It will be appreciated that a single sequence can align differently with other sequences and hence, can have different percent sequence identity values over each aligned region. It is noted that the percent identity value is usually rounded to the nearest integer.

The alignment of two or more sequences to determine percent sequence identity is performed using the algorithm described by Altschul et al. (1997, *Nucleic Acids Res.*, 25:3389-3402) as incorporated into BLAST (basic local alignment search tool) programs, available at ncbi.nlm.nih.gov on the World Wide Web. BLAST searches can be performed to determine percent sequence identity between a first nucleic acid and any other sequence or portion thereof aligned using the Altschul et al. algorithm. BLASTN is the program used to align and compare the identity between nucleic acid sequences, while BLASTP is the program used to align and compare the identity between amino acid sequences. When utilizing BLAST programs to calculate the percent identity between a sequence of the invention and another sequence, the default parameters of the respective programs are used.

Constructs containing such nucleic acids also are provided. Constructs, including expression vectors, are commercially available and/or can be produced by recombinant DNA technology methods routine in the art. A construct containing nucleic acid encoding one or more polypeptides also can have elements necessary for expression operably linked to such a nucleic acid, and further can include sequences such as those encoding a selectable marker (e.g., an antibiotic resistance gene), and/or those that can be used in purification of a polypeptide (e.g., 6×His tag). Elements necessary for expression include nucleic acid sequences that direct and regulate expression of coding sequences. One example of an element necessary for expression is a promoter sequence. Elements necessary for expression also can include introns, enhancer sequences, response elements, or inducible elements that modulate expression of a coding sequence. Elements necessary for expression can be of bacterial, yeast, insect, mammalian, or viral origin and vectors can contain a combination of elements from different origins. As used herein, operably linked means that a promoter and/or other regulatory element(s) are positioned in a construct relative to a coding sequence in such a way as to direct or regulate expression of the coding sequence. Many methods for introducing nucleic acids into cells are well known to those skilled in the art and include, without limitation, calcium phosphate precipitation, electroporation, heat shock, lipofection, microinjection, and viral-mediated nucleic acid transfer.

The nucleic acids described herein (e.g., in constructs) can be introduced into cells to thereby generate recombinant cells. The term "recombinant cell" refers not only to the particular cell into which the nucleic acid has been introduced but also to the progeny of such a cell. A recombinant cell can be a prokaryotic cell or a eukaryotic cell. For example, nucleic acids can be expressed in bacterial cells such as *E. coli*, or in insect, yeast or mammalian cells (such as Chinese hamster ovary cells (CHO) or COS cells). In addition, the cell can be an erythroid cell, or any other eukaryotic cell into which nucleic acids encoding TR2/TR4 polypeptides and nucleic acids encoding one or more of the other co-repressors identified herein can be introduced. Other suitable host cells that can be made recombinant are known to those skilled in the art.

The methods described herein for manipulating nucleic acids in order to express the desired combination of polypeptides require nothing more than standard molecular biology techniques that are well known in the art. Such routine molecular biology techniques are described, for example, in *Molecular Cloning: A Laboratory Manual*, Sambrook et al., Cold Spring Harbor Press (2001); and in *PCR Primer: A Laboratory Manual*, 1995, Dieffenbach & Dveksler, Eds., Cold Spring Harbor Laboratory Press, Cold Spring Harbor, N.Y.

Compounds for Use in the Screening Methods

Any number of different compounds can be screened in the methods described herein. Representative compounds include, for example, small molecules, polypeptides, synthetic compounds, naturally-occurring compounds, antibodies, antigen-binding fragment, or antigens.

Compounds that can be screened in the methods herein can include antibodies. As used herein, the term "antibody" is used in the broadest sense and includes fully assembled antibodies, monoclonal antibodies, polyclonal antibodies, multispecific antibodies (including bispecific antibodies), antibody fragments that can bind an antigen (including, Fab', F'(ab)2, Fv, single chain antibodies, diabodies), and recombinant peptides comprising the foregoing as long as they exhibit the desired biological activity. Multimers or aggregates of intact molecules and/or fragments, including derivatized multimers, aggregates or fragments, are contemplated. Antibodies of any isotype class or subclass, including IgG, IgM, IgD, IgA, and IgE, IgG1, IgG2, IgG3, IgG4, IgA1 and IgA2, or any allotype, also are contemplated.

In addition, compounds used in the screening methods described herein can include nucleic acids (e.g., oligonucleotides) or pharmaceutically acceptable salts thereof. Nonlimiting examples include antisense oligonucleotides, triplex oligonucleotides, ribozymes/deoxyribozymes (DNAzymes), small-interfering RNAs/RNAi, short hairpin RNA, aptamers, ribozymes or decoy oligonucleotides.

For example, small molecule libraries (e.g., chemical libraries, natural product libraries) can be obtained from various commercial sources, while other types of libraries (e.g., combinatorially generated nucleic acid or peptide libraries), can be generated using known methods. Simply by way of example, large combinatorial libraries of compounds can be constructed by the encoded synthetic libraries (ESL) methods described in WO 95/12608, WO 93/06121, WO 94/08051, WO 95/35503 and WO 95/30642. Peptide libraries can also be generated by phage display methods (see, e.g., WO 91/18980). Compounds to be screened can also be obtained from governmental or private sources including, e.g., the DIVERSet E library from ChemBridge Corporation (San Diego, Calif.), the National Cancer Institute's (NCI) Natural Product Repository, Bethesda, Md., the NCI Open Synthetic Compound Collection; Bethesda, Md., or NCI's Developmental Therapeutics Program.

Using Compounds that Inhibit the Interactions and/or De-repress the Human Gamma-Globin Gene in Pharmaceutical Compositions Compounds identified in the screening methods described herein or compounds that are already known inhibitors of DNMT1 or LSD-1 can be used to treat a beta-globin disorder in a mammal (e.g., a human). Beta-globin disorders, sometimes referred to as hemoglobinopathies, include any disorder associated with an alteration in the amount, structural integrity, or function of adult hemoglobin (i.e., beta-globin). Hemoglobinopathies include, but are not limited to, beta-thalassemia including beta0-(major) and beta+-(minor) thalassemia, and sickle cell disease including sickle cell anemia and sickle thalassemia.

As indicated herein, compounds that stimulate (or de-repress) the human gamma-globin gene can be screened from libraries, or compounds that are known to inhibit any of the co-repressors can be used. For example, a number of inhibitors of LSD-1 are known in the art, including, without limitation, tranylcypromine, derivatives of tranylcypromine (see, for example, Binda et al., 2010, *J. Am. Chem. Soc.*, 132:6827-33), analogues of tranylcypromine (see, for example, Genelkebir et al., 2011, *Bioorg. Med. Chem.*, [in press]), polyamine analogues, and a 2-PCPA derivative. In addition, a number of inhibitors of DNMT1 are known in the art, including, without limitation, doxorubicin, SGI-110 or SGI-1036, disulfuram, azacytidine, and decitabine.

Such compounds can be administered in an effective amount to an individual suffering from a beta-globin disorder. Typically, an effective amount is the amount that de-represses the gamma-globin promoter and results in an increase in the expression of the gamma-globin gene in a cell or population of cells without inducing any adverse effects. For example, an effective amount or a therapeutically effective amount or dose of a compound refers to the amount of compound that results in amelioration of symptoms or a prolongation of survival in a subject. Toxicity and therapeutic efficacy of such compounds can be determined by standard pharmaceutical procedures in cell cultures or experimental animals, e.g., by determining the LD50 (the dose lethal to 50% of the population) and the ED50 (the dose therapeutically effective in 50% of the population). The dose ratio of toxic to therapeutic effects is the therapeutic index, which can be expressed as the ratio LD50/ED50. Compounds that exhibit high therapeutic indices are preferred.

In certain embodiments, a compound as described herein can be administered along with a second therapeutic agent. See, for example, Atweh et al., 2010, *Hematol. Oncol. Clin. North Am.*, 24:1131-44. Representative second therapeutic agents include, for example, hydroxyurea, butyrate analogs, and 5-azacytidine, which have been shown to increase gamma-globin production, Gardos channel inhibitors, which inhibit dehydration of red blood cells, and/or hematopoietic growth factors such as erythropoietin and analogs thereof, mimetic peptides, mimetic antibodies, hypoxia-inducible factor (HIF) inhibitors, GM-CSF, and IL-3. The use of a compound in conjunction with a second therapeutic agent may facilitate reducing the required dosage of the second therapeutic agent to avoid pharmacokinetic or toxicity associated therewith.

Continuous formation and destruction of irreversibly sickled cells contributes significantly to the severe hemolytic anemia that occurs in patients with sickle cell disease. The anemia of sickle cell can be even more severe if erythropoiesis is suppressed. For example, folic acid and vitamin B12 are required for proper cell division; and deficiency in these nutrients leads to enlarged blood cells (megaloblastic cells), which are destroyed in the marrow, thus causing anemia due to ineffective erythropoiesis. Further, a deficiency in iron, which is necessary for functional heme production, further aggravates the anemia. Therefore, in yet another embodiment, a compound as described herein is administered with yet another agent selected from the group consisting of folic acid, vitamin B12, and an iron supplement, e.g., ferrous gluconate.

In another embodiment, a compound as described herein can be used to treat cells ex vivo to induce gamma-globin production. The cells are then transfused into an individual suffering from a beta-globin disorder and in need of treatment. In a particular embodiment, the cells are bone marrow cells. The bone marrow cells can be derived from the individual (autologous) or from a matched donor (allogenic). Following treatment of the cells with a compound as described herein, the cells can be delivered to the individual in conjunction with current blood transfusions, e.g., for treatment of sickle cell disease.

Pharmaceutical Compositions and Routes of Administration

The compounds identified in the screening methods described herein or compounds that are already known to be inhibitors of DNMT1 or LSD-1 can be formulated with a pharmaceutically acceptable carrier for delivery to an individual. The particular formulation, will be dependent upon a variety of factors, including route of administration, dosage and dosage interval of a compound the sex, age, and weight of the individual being treated, the severity of the affliction, and the judgment of the individual's physician. As used herein, "pharmaceutically acceptable carrier" is intended to include any and all excipients, solvents, dispersion media, coatings, antibacterial and anti-fungal agents, isotonic and absorption delaying agents, and the like, compatible with administration. The use of such media and agents for pharmaceutically acceptable carriers is well known in the art. Except insofar as any conventional media or agent is incompatible with a compound, use thereof is contemplated.

Pharmaceutically acceptable carriers for delivering compounds are well known in the art. See, for example *Remington: The Science and Practice of Pharmacy*, University of the Sciences in Philadelphia, Ed., 21$^{st}$ Edition, 2005, Lippincott Williams & Wilkins; and *The Pharmacological Basis of Therapeutics*, Goodman and Gilman, Eds., 12$^{th}$ Ed., 2001, McGraw-Hill Co. The type of pharmaceutically acceptable carrier used in a particular formulation can depend on various factors, such as, for example, the physical and chemical properties of the compound, the route of administration, and the manufacturing procedure. Pharmaceutically acceptable carriers are available in the art, and include those listed in various pharmacopoeias. See, for example, the U.S. Pharmacopeia (USP), Japanese Pharmacopoeia (JP), European Pharmacopoeia (EP), and British pharmacopeia (BP); the U.S. Food and Drug Administration (FDA) Center for Drug Evaluation and Research (CDER) publications (e.g., Inactive Ingredient Guide (1996)); and Ash and Ash, Eds. (2002) Handbook of Pharmaceutical Additives, Synapse Information Resources, Inc., Endicott, N.Y.

A pharmaceutical composition that includes a compound as described herein is typically formulated to be compatible with its intended route of administration. Suitable routes of administration include, for example, oral, rectal, topical, nasal, pulmonary, ocular, intestinal, and parenteral administration. Routes for parenteral administration include intravenous, intramuscular, and subcutaneous administration, as well as intraperitoneal, intra-arterial, intra-articular, intracardiac, intracisternal, intradermal, intralesional, intraocular, intrapleural, intrathecal, intrauterine, and intraventricular administration.

For intravenous injection, for example, the composition may be formulated as an aqueous solution using physiologically compatible buffers, including, for example, phosphate, histidine, or citrate for adjustment of the formulation pH, and a tonicity agent, such as, for example, sodium chloride or dextrose. For transmucosal or nasal administration, semisolid, liquid formulations, or patches may be preferred, optionally containing penetration enhancers, which are known in the art. For oral administration, a compound can be formulated in liquid or solid dosage forms, and also formulation as an instant release or controlled/sustained release formulations. Suitable dosage forms for oral ingestion by an individual include tablets, pills, hard and soft shell capsules, liquids, gels, syrups, slurries, suspensions, and emulsions. The compounds may also be formulated in rectal compositions, such as suppositories or retention enemas, e.g., containing conventional suppository bases such as cocoa butter or other glycerides.

Solid oral dosage forms can be obtained using excipients, which can include fillers, disintegrants, binders (dry and wet), dissolution retardants, lubricants, glidants, anti-adherants, cationic exchange resins, wetting agents, antioxidants, preservatives, coloring, and flavoring agents. These excipients can be of synthetic or natural source. Examples of such excipients include cellulose derivatives, citric acid, dicalcium phosphate, gelatine, magnesium carbonate, magnesium/sodium lauryl sulfate, mannitol, polyethylene glycol, polyvinyl pyrrolidone, silicates, silicium dioxide, sodium benzoate, sorbitol, starches, stearic acid or a salt thereof, sugars (e.g., dextrose, sucrose, lactose), talc, tragacanth mucilage, vegetable oils (hydrogenated), and waxes. Ethanol and water may serve as granulation aides. In certain instances, coating of tablets with, for example, a taste-masking film, a stomach acid resistant film, or a release-retarding film is desirable. When a capsule is preferred over a tablet, the drug powder, suspension, or solution thereof can be delivered in a compatible hard or soft shell capsule.

Compounds described herein can be administered topically, such as through a skin patch, a semi-solid, or a liquid formulation, for example a gel, a (micro-) emulsion, an ointment, a solution, a (nano/micro)-suspension, or a foam. The penetration of the drug into the skin and underlying tissues can be regulated, for example, using penetration enhancers; the appropriate choice and combination of lipophilic, hydrophilic, and amphiphilic excipients, including water, organic solvents, waxes, oils, synthetic and natural polymers, surfactants, emulsifiers; by pH adjustment; and the use of complexing agents. For administration by inhalation (e.g., via the mouth or nose), compounds can be delivered in the form of a solution, suspension, emulsion, or semisolid aerosol from pressurized packs, or a nebuliser, usually with the use of a propellant, e.g., halogenated carbons.

Compounds described herein also can be formulated for parenteral administration (e.g., by injection). Such formulations are usually sterile and, can be provided in unit dosage forms, e.g., in ampoules, syringes, injection pens, or in multi-dose containers, the latter usually containing a preservative. The formulations may take such forms as suspensions, solutions, or emulsions in oily or aqueous vehicles, and may contain other agents, such as buffers, tonicity agents, viscosity enhancing agents, surfactants, suspending and dispersing agents, antioxidants, biocompatible polymers, chelating agents, and preservatives. Depending on the injection site, the vehicle may contain water, a synthetic or vegetable oil, and/or organic co-solvents. In certain instances, such as with a lyophilized product or a concentrate, the parenteral formulation would be reconstituted or diluted prior to administration. Polymers such as poly(lactic acid), poly(glycolic acid), or copolymers thereof, can serve as controlled or sustained release matrices, in addition to others well known in the art. Other delivery systems may be provided in the form of implants or pumps.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Part A

Example 1

Antibodies

Rabbit polyclonal antibodies against TR2 and TR4 generated and purified as described previously (Tanabe et al., 2007, *EMBO J.*, 26:2295-306) was further purified with Melon Gel IgG Spin Purification Kit (Thermo Scientific). For co-immunoprecipitaion and Western blotting, antibodies against DNMT1 (sc-20701), MTA1 (sc-10813), MTA2 (sc-9447), HDAC2 (sc-7899), Mi213 (sc-8774), RbAp46/48 (sc-8272), MBD2 (sc-12444), MBD3 (sc-9402), CoREST (sc-23448), LSD1 (sc-67272), and TIF113 (sc-33186) were obtained from Santa Cruz Biotechnology, and antibodies against HDAC1 (ab7028), p66 (ab76924), HDAC3 (ab7030), and LSD1 (ab17721) were obtained from Abcam, and an antibody against TIF1β (K0075-04) was obtained from US Biological. For ChIP assays, the same Abcam antibodies against HDAC1, HDAC3, and LSD1 were used, as well as antibodies against CoREST (ab24166), TIF1β (ab10483), DNMT1 (ab16632), and Mi2β (ab72418) as well as normal rabbit IgG (ab46540) from Abcam, and an MTA1 (sc-10813) antibody from Santa Cruz Biotechnology.

Example 2

Chromatin Immunoprecipitation (ChIP) Assays

ChIP assays were performed essentially as described (Frietze et al., 2010, *PLoS One,* 5:e15082; O'Geen et al., 2010, BMC Genomics, 11:689) with minor modifications. MEL cells were harvested before or after differentiation induction (with 2% DMSO for 5 days). Differentiation was confirmed by benzidine staining of the cells (>90%). $10^8$ cells were washed twice with PBS, and then incubated with 1% formaldehyde (Polysciences) in 50 ml PBS at room temperature for 10 min with gentle shaking, followed by addition of 0.125 M glycine and continued incubation for 5 min. For ChIP assay with TR2 or TR4 antibody, cells were treated with 2 mM ethylene glycolbis(succinimidyl succinate) (EGS) (Pierce) in 50 ml PBS at room temperature for 30 min, prior to the addition of formaldehyde (Polysciences) as described previously (Zeng et al., 2006, *Biotechniques*, 41:694,696, 698). All procedures were carried out at 0-4° C. unless specifically stated otherwise. After lysing the cells with a Dounce homogenizer in 10 ml of cell lysis buffer (5 mM PIPES, pH8.0, 85 mM KCl, 1% Igepal) with protease inhibitors (10 µg/ml aprotinin, 10 µg/ml leupeptin, and 1 mM PMSF), nuclei were collected by centrifugation (at 13,000×g for 5 min) and then lysed by incubation in 2 ml of ChIP lysis buffer (50 mM Tris, pH8.0, 10 mM EDTA, 1% SDS) containing the protease inhibitors for 30 min. After shearing DNA by sonication, the lysate was clarified by centrifugation (at 10,000×g for 10 min) and then divided into 20 µl aliquots for immunoprecipitation, to which 500 µl of IP dilution buffer (50 mM Tris, pH 7.4, 150 mM NaCl, 1% Igepal, 0.25% deoxycholic acid, 1 mM EDTA, and protease inhibitors) was added. After addition of 1-10 µg of antibody to the 500 µl of lysate (equivalent to $10^6$ cells) and incubation for 12 hr, 15 µl of protein A agarose beads (Millipore) were added to the lysate and mixed by rotation for 2 hr. The beads were washed with 1 ml IP dilution buffer without protease inhibitors with rotation 3 times for 5 min, and then once with PBS. Protein-DNA cross-linked material was then eluted by vortexing in 150 µl of elution buffer (50 mM NaHCO$_3$, 1% SDS) for 30 min at room temperature. After removing the beads by centrifugation (190×g for 5 min at room temperature), 5 M NaCl was added to a final concentration of 0.54 M.

After heating the samples to 67° C. for 2 hr to reverse the cross-linking, the DNA was purified using a QIAquick PCR Purification Kit (Qiagen), and then subjected to real-time quantitative PCR assay with SYBR Green Master Mix (Applied Biosystems) on an ABI Prism 7000 (Applied Biosystems). PCR assays were performed in triplicates from at least two independent immunoprecipitations. The abundance of specifically immunoprecipitated DNA relative to input was determined from the threshold cycle numbers of the two samples using experimentally determined amplification efficiencies for primer sets. Following PCR primers were used to quantify murine genomic sequences: embryonic epsilonY-globin promoter, 5'-GAA AGA ATA CCT CCA TAT CTA ATG TGC AT-3' (SEQ ID NO:1) and 5'-CTG CAT TAT TCT TTG AAG CTA TTG GT-3' (SEQ ID NO:2); embryonic betaH1-globin promoter, 5'-GGA CCC CAC CCC TGT CTT-3' (SEQ ID NO:3) and 5'-TTA CCC CTC CCC AGG ACT CT-3' (SEQ ID NO:4); adult beta$^{major}$-globin promoter, 5'-GAA GCC TGA TTC CGT AGA GC-3' (SEQ ID NO:5) and 5'-CAA CTG ATC CTA CCT CAC CTT ATA TGC-3' (SEQ ID NO:6); intergenic region between betaH1- and beta$^{major}$-globin genes, 5'-CGG GAT GGG CAT TAA AGG TA-3' (SEQ ID NO:7) and 5'-AAC AAC CTG TGT CAG AAG CAG ATG-3' (SEQ ID NO:8); SCAP gene promoter; 5'-CGC GGT CCG GTG TTT G-3' (SEQ ID NO:9) and 5'-GGA AAG GTA GGA GTT GAG AGG TGA A-3' (SEQ ID NO:10).

Example 3

Plasmid Vectors

The 23-amino acid biotinylation tag sequence (de Boer et al., 2003, *PNAS USA*, 100:7480-5) was cloned into the NcoI site overlapping the translation initiation codon of the N-terminally FLAG-tagged TR2 and TR4 cDNAs cloned in pBluescript II SK+ (Tanabe et al., 2002, *EMBO J.*, 21:3434-42). After introducing an EagI linker into the XhoI site of the vector multiple cloning site at the C-terminus of the biotin-FLAG-TR2 or biotin-FLAG-TR4 construct, the tagged cDNAs were released from the vector by EagI digestion and cloned into a unique NotI site in the erythroid specific expression vector, pEV3neo (Needham et al., 1992, *Nuc. Acids Res.*, 20:997-1003).

Example 4

MEL Cell Culture and Transfections

Mouse erythroleukemia (MEL) cells were cultured and induced to differentiate, as previously described (Antoniou, 1991, In *Methods in Molecular Biology: Gene Transfer and Expression Protocols*; Ed., Murray, 7:421-34, Humana, Clifton, N.J.; Rodriquez et al., 2005, *EMBO J.*, 24:2354-66). Tagged TR2 and TR4 in the pEV3neo expression vector were transfected into MEL cells stably transformed with the BirA biotin ligase, as previously described (de Boer et al., 2003, *PNAS USA*, 10:7480-5). Clones were obtained by G418 and puromycin selection (the latter selects for BirA-expressing cells) and screened by immunoblotting for efficient expression and biotinylation of tagged TR2 and TR4.

Example 5

Fractionation of Nuclear Extract by Superose 6 Gel Filtration

Nuclear extracts were prepared essentially as previously described (de Boer et al., 2003, *PNAS USA*, 10:7480-5; Rodriguez et al., 2006, *Methods Mol. Biol.*, 338:305-23). Size fractionation of MEL nuclear extracts using an analytical Superose 6 column was carried out as previously described (Rodriguez et al., 2005, *EMBO J.*, 24:2354-66; Rodriguez et al., 2006, *Methods Mol. Biol.*, 338:305-23). Preparative size fractionation by gel filtration was done by injecting 40 mg of nuclear extract protein (in 5 ml) into a preparative grade Superose 6 XK50/600 column connected to an AKTA FPLC system (GE Healthcare Life Sciences) equilibrated in running buffer (20 mM HEPES pH 7.9, 0.5 mM EGTA, 1 mM MgCl$_2$, 200 mM KCl, 10% glycerol). Gel filtration was carried out at 4° C., and 10 ml fractions were collected and concentrated by TCA precipitation for analysis by immunoblotting, or pooled and bound directly to streptavidin beads, as described below. A detailed protocol for preparative Superose 6 gel filtration has already been described (Rodriguez et al., 2006, *Methods Mol. Biol.*, 338:305-23).

Example 6

Binding to Streptavidin Beads

Direct binding of nuclear extracts to streptavidin beads was carried out as described (de Boer et al., 2003, *PNAS USA*, 100:7480-5; Rodriguez et al., 2006, *Methods Mol. Biol.*, 338: 305-23). Binding of fractions following preparative gel filtration was done by pooling fraction numbers 20 through 38 and adjusting KCl and NP-40 concentrations to 150 mM and 0.3%, respectively. Diluted, pooled fractions were then divided into 50 ml Falcon tubes, to which Dynabeads M-280 streptavidin (Invitrogen), pre-blocked as described previously (de Boer et al., 2003, *PNAS USA*, 100:7480-5), was added for overnight incubation at 4° C. on a rotating wheel. Approximately 10 µl of resuspended beads were used per original 10 ml fraction. Following overnight incubation, the beads were pooled and washed as described previously (de Boer et al., 2003, *PNAS USA*, 100:7480-5). Bound proteins were eluted with 1× Laemmli sample buffer (50 µl of sample buffer per 20 µl of beads), and then resolved by SDS-PAGE. Alternatively, bound proteins were trypsinized directly on the beads and processed for mass spectrometry as described below.

Example 7

Mass Spectrometry

Proteins eluted from streptavidin beads were resolved by SDS-PAGE and gel lanes were cut into slices using an automatic gel slicer and subjected to in-gel trypsinization, essentially as described (Shevchenko et al., 1996, *Anal. Chem.*, 68:850-8). Alternatively, bound proteins were trypsinized on the beads after resuspending in 50 mM ammonium bicarbonate and adding trypsin (sequencing grade, Promega) to approximately 60 ng/mg of total protein, followed by overnight incubation at 37° C. (Rybak et al., 2005, *Nat. Methods*, 2:291-8). The supernatant containing the trypsinized peptides was then recovered by magnetically removing the beads. Peptides released by in-gel or on-bead trypsinization were analyzed by nano LC-MS/MS performed on either a CapLC system (Waters, Manchester, UK) coupled to a Q-ToF Ultima mass spectrometer (Waters, Manchester, UK), operating in positive mode and equipped with a Z-spray source, or a 1100 series capillary LC system (Agilent Technologies) coupled to an LTQ-Orbitrap or LTQ-FT-MS mass spectrometer (both Thermo) operating in positive mode and equipped with a nanospray source. Peptides were trapped and separated on a Jupiter™ C18 reversed phase column (Phenomenex) using a linear gradient from 0 to 80% B (A=0.1 M acetic acid; B=80% (v/v) acetonitrile, 0.1 M acetic acid) using a splitter. The column eluate was directly sprayed into the ESI source of the mass spectrometer. Mass spectra were acquired in continuum mode; fragmentation of the peptides was performed in data-dependent mode.

Example 8

Data Analysis and Protein Identification

Peak lists were automatically created from raw data files using the ProteinLynx Global Server software (version 2.0; Waters, Manchester, UK) for Q-ToF spectra and the Mascot Distiller software (version 2.0; MatrixScience, London, UK) for LTQ-Orbitrap and LTQ-FT-MS spectra. The Mascot search algorithm (version 2.0, MatrixScience, London, UK) was used for searching the NCBI nr database (release NCBI nr 20060106; taxonomy *M. musculus*). The Mascot score cut-off value for a positive hit was set to 65. Individual peptide MS/MS spectra with Mowse scores below 40 were checked manually and either interpreted as valid identifications or discarded. Identified proteins listed as NCBI nr database entries were screened to identify proteins that were also identified in mass spectrometry experiments from control BirA-expressing cells (de Boer et al., 2003, *PNAS USA*, 100:7480-5). These were removed as background binding proteins. The remaining proteins were classified according to Gene Ontology criteria as listed for each protein in the Mouse Genome Informatics database ("informatics.jax.org/" on the World Wide Web) and were then grouped according to a highly representative identifier based on Biological Process or Molecular Function.

Example 9

Streptavidin Pull-Down Assay

Nuclear extracts were prepared as described previously (72) from MEL cells expressing biotin-tagged TR2 and TR4. Pre-blocked Dynabeads M-270 streptavidin (Invitrogen) was incubated with the nuclear extracts containing biotin-tagged TR2 and TR4 proteins for 1 hr at 4° C. with rotation according to the manufacturer's instructions. 150 µg of nuclear extract protein was used for each assay. After washing the beads with buffer (10 mM HEPES-KOH, pH 9.0, 250 mM KCl, 1.5 mM $MgCl_2$, 0.25 mM EDTA, 20% glycerol, 0.3% NP-40, 1 mM PMSF) three times, bound proteins were eluted from the beads by boiling in 1× Laemmli sample buffer, and then subjected to SDS-PAGE followed by immunoblotting.

Example 10

Immunoprecipitation

Antibodies were coupled to Dynabeads protein G (Invitrogen) by incubating for 2 hr at 4° C. with rotation according to the manufacturer's instructions. The beads were then incubated with nuclear extracts (150 µg protein) prepared from untransfected MEL cells for 2 hr at 4° C. After washing the beads with ice-cold phosphate buffered saline (PBS) three times, immunoprecipitated proteins were eluted by boiling in 1× Laemmli sample buffer and then subjected to immunoblotting.

Example 11

Immunoblotting

After SDS-PAGE, proteins were transferred to a nitrocellulose membrane (Li-Cor) and probed with specific primary antibodies (described above) and fluorescence-conjugated secondary antibodies (Li-Cor). Proteins were visualized on the Odyssey Infrared Imaging System (Li-Cor).

Example 12

Binding of TR2 and TR4 to the Embryonic Beta-Type Globin Promoters in Adult Erythroid Cells Previous biochemical and genetic studies suggested that a TR2/TR4 heterodimer directly repressed the embryonic and fetal beta-type globin genes in adult erythroid cells through direct repeat (DR) elements in their promoters. In order to provide further evidence for this contention, chromatin immunoprecipitation (ChIP) assays were performed to demonstrate in vivo TR2/TR4 binding to the embryonic beta-type globin promoters in adult erythroid cells. To do so, the murine erythroleukemia (MEL) cell line was used, the only established cell line with a gene expression profile typical of adult erythroid cells, where the embryonic epsilonY and betaH1 genes, orthologues of human embryonic epsilon- and fetal gamma-globin genes, respectively (which both possess DR sequences in their promoters), are silenced.

Figure 1:
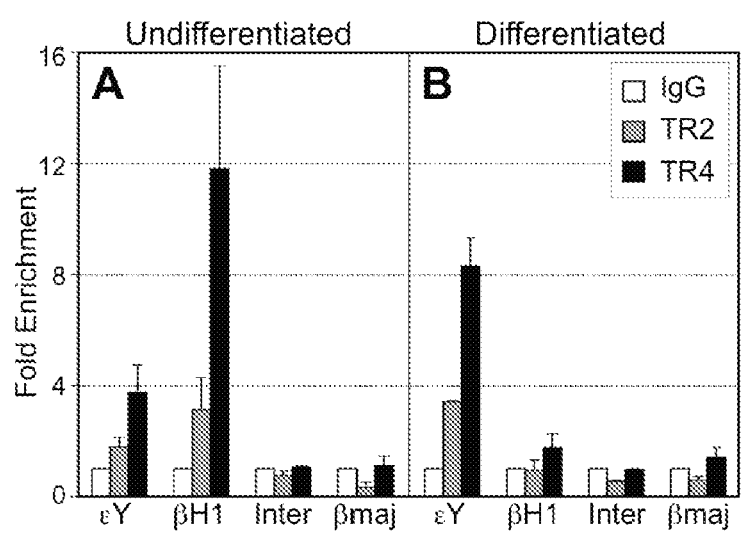
FIG. 1 is a graph showing that TR2/TR4 binds to the mouse embryonic 13-type globin gene promoters in adult erythroid (MEL) cells. Binding of TR2 and TR4 to the proximal promoter regions, including the DR sequences, of the murine embryonic epsilonY- and betaH1-globin genes in undifferentiated (Panel A) or differentiated (Panel B) MEL cells was analyzed by ChIP assay. For negative controls, the proximal promoter of the adult beta$^{major}$-globin gene (βmaj; which has no DR sequence), as well as an intergenic region (Inter) between the betaH1 and beta$^{major}$ genes (5.9 kbp 5' to the beta$^{major}$ promoter) were also analyzed. Error bars represent standard errors of the mean (SEM).

Cross-linked chromatin from MEL cells before and after differentiation induction with DMSO was prepared and analyzed for TR2 and TR4 binding to the promoters of the embryonic and adult genes. In undifferentiated MEL cells, binding of both TR2 and TR4 to both epsilonY- and betaH1-promoters was clearly and reproducibly detected in multiple experiments, whereas no binding was detectable to the promoter of the adult beta$^{major}$-globin gene, or to an intergenic region between the betaH1 and beta$^{major}$ genes (FIG. 1A). In differentiated MEL cells, binding of TR2 and TR4 were reproducibly detected at the epsilonY-promoter, whereas binding to the betaH1-gene promoter was not reproducibly detected (FIG. 1B).

Example 13

Expression of Biotin-Tagged TR2 and TR4 in MEL Cells

Figure 2:
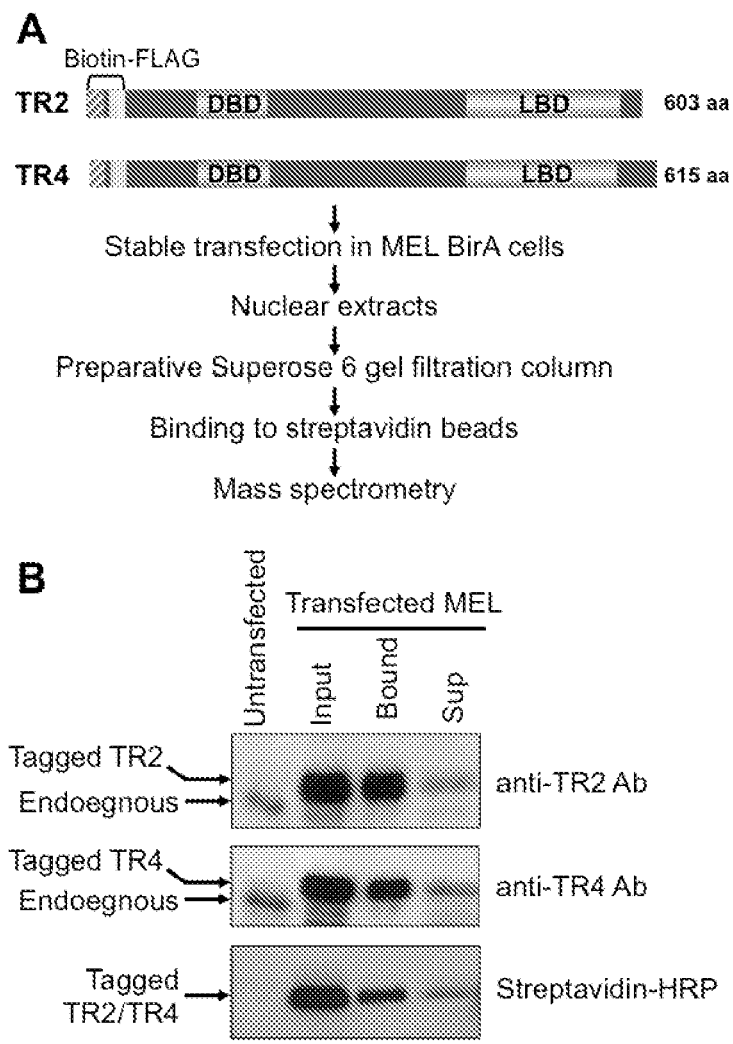
FIG. 2 shows the experimental strategy for characterizing TR2/TR4-interacting proteins in MEL cells. Panel A shows that TR2 and TR4 cDNA were tagged with biotinylation and FLAG sequences, and then stably transfected into BirA-expressing MEL cells. DBD: DNA binding domain; LBD: ligand binding domain. Panel B shows the efficient biotinylation and recovery of tagged TR2 and TR4 from transformed MEL cells. Untransfected MEL and input lanes indicate the relative abundance of endogenous and biotin-tagged transfected TR2 and TR4 proteins. For input and supernatant (Sup) lanes, the same volumes of nuclear extracts before and after streptavidin-bead binding were loaded. Endogenous and transfected TR2 and TR4 proteins were detected by immunoblotting using anti-TR2 and anti-TR4 antibodies (upper and middle panels) (see, also, Tanabe et al., 2007, EMBO J., 26:2295-306). Biotin tagged TR2 and TR4 were detected using HRP-conjugated streptavidin (bottom panel).

In order to investigate details of the molecular mechanisms underlying silencing by TR2/TR4 of the embryonic and fetal beta-type globin genes in adult erythroid cells, it was planned to identify molecules that physically interact with TR2/TR4 and are thereby recruited to those genes to elicit stage-specific silencing. Both biotin-FLAG-tagged TR2 and TR4 were transfected into MEL cells expressing the BirA biotin ligase to establish stably transformed cell lines (FIG. 2A), as it has been previously shown that TR2 and TR4 preferentially heterodimerize and that the TR2/TR4 heterodimer forms the core of the DRED complex which binds with high affinity to the DR sequences in the human epsilon- and gamma-globin promoters. It was further reasoned that affinity tagging both proteins would help enrich for the DRED complex during protein complex purification. Immunoblot analysis of double transfectants using TR2 and TR4 antibodies showed that the tagged orphan receptors were expressed at higher levels than their endogenous counterparts, possibly as a consequence of using the heterologous human beta-globin gene promoter of the pEV3neo vector to direct TR2 and TR4 expression (FIG. 2B). In fact, the forcibly expressed, tagged TR2 and TR4 appeared to repress endogenous receptor levels, suggesting a potential negative transcriptional feedback loop. The efficiency of TR2 and TR4 biotinylation was tested by direct binding of nuclear extracts to streptavidin beads and it was found that 80-90% of the tagged protein was biotinylated by comparison of band intensities in the input and supernatant (Sup) lanes (FIG. 2B).

Example 14

Identification of TR2/TR4 Interacting Proteins by Mass Spectrometry

Figure 3:
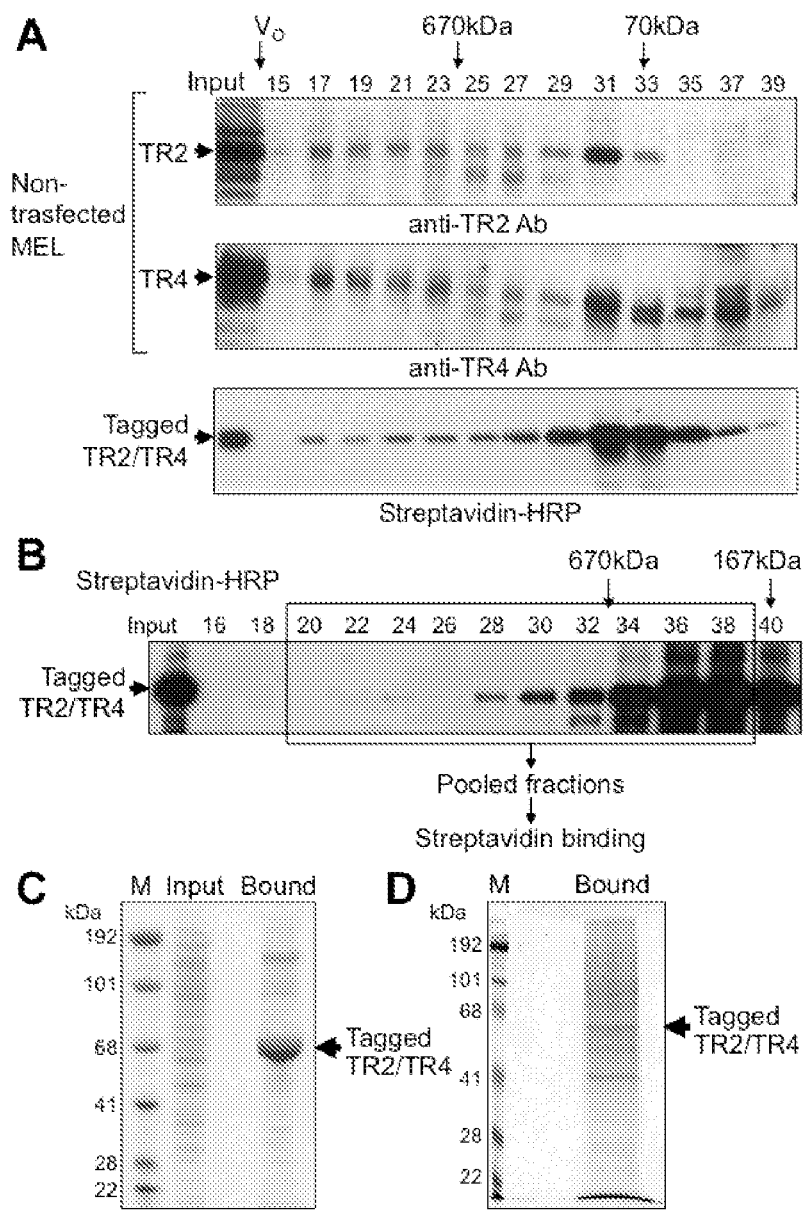
FIG. 3 shows the recovery of proteins that co-purify with biotinylated TR2/TR4. Panel A shows the size fractionation of nuclear extracts by analytical Superose 6 gel filtration. Fractions from induced (wild type) MEL cells were analyzed by immunoblotting with anti-TR2 (top panel) or anti-TR4 (middle panel) antibodies. Fractions from induced MEL cells transformed with biotin-tagged TR2 and TR4 were analyzed by affinity-blotting with HRP-conjugated streptavidin (bottom panel). The void volume ($V_0$) and the elution of two molecular weight markers are indicated with arrows. Panel B shows the fractionation of biotin-tagged TR2 and TR4 on a preparative Superose 6 column. Biotinylated TR2/TR4 proteins were detected by affinity blotting with HRP-streptavidin. Fractions that were pooled for streptavidin binding and mass spectrometric analysis are boxed. Panel C shows the coomassie-stained SDS-polyacrylamide (4-12% gradient) gel of proteins bound to streptavidin beads from unfractionated MEL nuclear extract. Unfractionated nuclear extract prepared from induced MEL cells transfected with tagged TR2 and TR4 was incubated with streptavidin beads, from which bound proteins were eluted with 1× Laemmli sample buffer for SDS-PAGE. The arrow indicates the migration position of tagged TR2 and TR4 proteins. M: molecular weight markers. Panel D shows the coomassie-stained SDS-polyacrylamide (8%) gel showing proteins bound to streptavidin beads from size-fractionated MEL nuclear extract. Proteins in size-fractionated nuclear extract from the transfected MEL cells were bound to and then eluted from streptavidin beads prior to SDS-PAGE.

Using size exclusion chromatography (with an analytical Superose 6 gel filtration column), the presence of TR2/TR4 was assessed in high molecular weight protein complexes in MEL nuclear extracts. The fractionation profiles of tagged TR2/TR4 proteins, as detected by streptavidin-HRP, were similar to those for the endogenous proteins in nuclear extracts from untransfected MEL cells (FIG. 3A). The majority of tagged TR2 and TR4 proteins elute in peaks equivalent to, or only slightly larger than, the molecular weight of the heterodimer (approximately 167 kDa, fraction 27 and higher), whereas less of the tagged protein elutes with massive (>670 kDa) molecular weight fractions. When larger scale streptavidin binding of biotin-tagged TR2/TR4 from MEL nuclear extracts was attempted and then the eluted material visualized by Coomassie staining, a strongly staining band migrating with a molecular weight consistent with that of the TR2 and TR4 monomers was observed, with other co-eluting proteins staining more weakly (FIG. 3C). This was also reflected in the mass spectrometric analysis of this same gel lane, showing that the vast majority of peptides identified were derived from TR2 and TR4, with little information regarding the identity of other co-eluted proteins.

On the basis of these initial observations and in order to enrich for the TR2/TR4 high molecular weight complexes, a preparative Superose 6 gel filtration column was employed with a matrix bed volume of 550 ml, thus allowing the fractionation of more than 40 mg of protein prepared from MEL nuclear extracts. Fractions with a molecular mass greater than that of the TR2/TR4 heterodimer were pooled and then bound to streptavidin beads (FIG. 3B). By Coomassie staining, numerous co-purified protein bands were observed on SDS polyacrylamide gels (FIG. 3D). The retained proteins were eluted by boiling, and then separated by SDS-PAGE followed by trypsinization of gel slices or trypsinized while still bound to the beads.

Peptides were identified by Q-TOF or LTQ-FT mass spectrometry in three separate experiments. After subtracting background protein binding, the remaining peptides were manually curated and the proteins were then grouped according to broadly representative Gene Ontology (GO) criteria. The TR2/TR4 heterodimer-interacting proteins identified by mass spectrometric analysis is shown in Table 1. Since the total number of peptides identified per protein provides some indication of its relative abundance, the number of peptides corresponding to each GO class was also graphically depicted as a percentage of the total number of peptides (e.g. FIG. 4 (shows experiment 1)). While, as anticipated, it was found that TR2 and TR4 were the most abundant proteins identified, a number of enzymes and accessory factors related to transcriptional regulation and chromatin remodeling/modification were co-purified with TR2 and TR4. Intriguingly, DNMT1 was found to be among the most abundant of these co-purifying proteins in all three experiments. A number of subunits of the NuRD repressor complex were also consistently identified in all experiments. In addition, a number of co-repressor proteins were identified that have been previously reported to interact with other nuclear receptors. These include TIF1beta, LSD1, and Sin3A. Other co-regulatory proteins for nuclear receptors, NonO (p5e), SFPQ (PSF) and PSPC1 (PSP1), which are less well characterized and also known as paraspeckle-associated proteins, were also identified in all mass spectrometric analyses. Co-activators HCF1 (Host Cell Factor 1), CAPER, and BRG1 were also identified in multiple experiments.

TABLE 1

| Protein Identity | Experiment #1 Peptides | | Experiment #2 Peptides | | Experiment #3 Peptides | |
|---|---|---|---|---|---|---|
| | Total$^a$ | % Coverage$^b$ | Total | % Coverage | Total | % Coverage |
| Orphan Nuclear Receptors | | | | | | |
| TR4 | 53 | 32.0% | 101 | 36.7% | 26 | 27.7% |
| TR2 | 28 | 9.7% | 22 | 22.5% | 9 | 17.3% |

TABLE 1-continued

| Protein Identity | Experiment #1 Peptides | | Experiment #2 Peptides | | Experiment #3 Peptides | |
|---|---|---|---|---|---|---|
| | Total[a] | % Coverage[b] | Total | % Coverage | Total | % Coverage |
| DNMT1 | 35 | 13.5% | 14 | 10.1% | 15 | 10.4% |
| NuRD complex | | | | | | |
| Mi2β | 1 | 1.1% | 4 | 5.3% | 6 | 4.4% |
| HDAC1 | 2 | 4.4% | — | — | 3 | 8.9% |
| HDAC2 | — | — | — | — | 2 | 4.9% |
| RbAp48 | 2 | 2.0% | 3 | 6.3% | 1 | 1.9% |
| RbAp46 | 2 | 2.0% | 3 | 6.8% | — | — |
| MTA1 | 7 | 8.7% | 1 | 1.7% | 1 | 1.8% |
| MTA2 | 2 | 2.8% | — | — | — | — |
| Co-repressors | | | | | | |
| TIF1β | 16 | 12.7% | 6 | 9.0% | 1 | 1.8% |
| LSD1 | — | — | — | — | 1 | 3.4% |
| NonO | 10 | 7.8% | 9 | 17.8% | 7 | 11.0% |
| SFPQ | 12 | 15.3% | 8 | 15.9% | 10 | 18.2% |
| PSPC1 | 1 | 3.3% | 3 | 7.8% | 2 | 4.6% |
| Sin3A | — | — | — | — | 1 | 1.1% |
| Co-activators | | | | | | |
| HCF1 | 4 | 2.5% | 2 | 1.4% | 1 | 0.8% |
| CAPER | — | — | 2 | 4.9% | 1 | 2.6% |
| BRG1 | 2 | 1.4% | — | — | 1 | 0.8% |
| Total | 388 | | 371 | | 229 | |

[a]Numbers of total peptide sequences for each protein identified in three independent mass spectrometry experiments are listed.
[b]% Coverage refers to percentage of the full-length sequence of each protein identified in these analyses.

Figure 4:
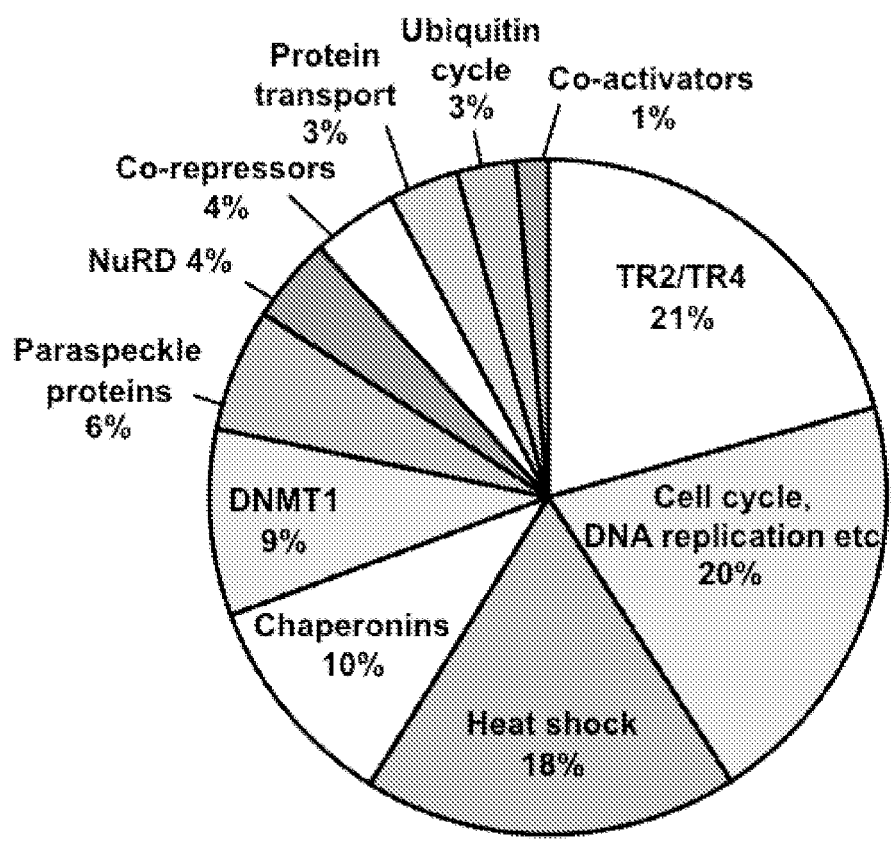
FIG. 4 is a graph showing the different classes of proteins identified by mass spectrometry as TR2/TR4-interacting proteins. The number of peptides corresponding to the different GO classes is presented as a percentage of the total number of peptides shown in mass spectrometry experiment #1 in Table 1.

Other classes of identified proteins included those involved in cellular functions related to cell cycle, cell division, DNA replication and recombination (broadly classified as Cell Cycle related), heat shock proteins, chaperonins, proteins involved in intracellular protein transport and in the ubiquitin cycle (FIG. 4). Interactions of nuclear receptors with heat shock proteins acting as chaperones are well characterized and these chaperones have been implicated in refolding and nuclear translocation of nuclear receptors. It is possible that co-purification of chaperonins, intracellular protein transporters, and ubiquitin cycle proteins is related to proper folding, intracellular localization and regulated degradation of TR2 and TR4.

Example 15

Interactions of Putative Co-Repressors with Biotin-Tagged TR2 and TR4

Figure 5:
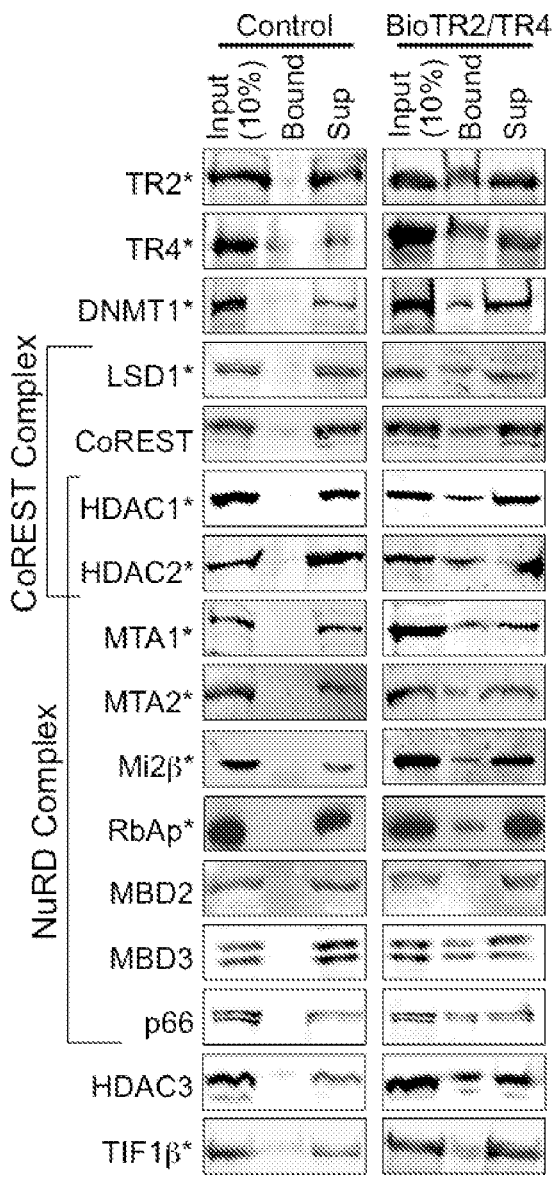
FIG. 5 shows the results of immunoblotting analysis of proteins precipitated with streptavidin beads from MEL cells expressing biotin-tagged TR2 and TR4. Nuclear extracts were prepared from induced MEL cells expressing the biotin ligase gene (BirA) without (control) or with biotin-tagged TR2 and TR4, and then incubated with streptavidin beads. 150 µg of nuclear extract protein was used in each binding reaction. Proteins precipitated with the beads (Bound), 10% of the input (15 µg protein), and 10% of supernatants (Sup) were subjected to SDS-PAGE followed by immunoblotting using antibodies that recognize the proteins shown to the left. TR2/TR4-interacting proteins identified by mass spectrometry are indicated by asterisks.

The association of TR2/TR4 with the NuRD repressor complex subunits (HDAC1/2, MTA1/2, Mi2beta, and RbAp46/48) as initially indicated by mass spectrometry was confirmed by immunoblotting of proteins recovered using streptavidin beads from nuclear extracts of MEL cells expressing biotin-tagged TR2 and TR4 (FIG. 5). In addition, other NuRD subunits, MBD3 and p66, which were not detected by mass spectrometry, were also confirmed by immunoblot analysis, whereas MBD2, was not detected by either mass spectrometry or immunoblotting.

The interactions between TR2/TR4 and DNMT1, LSD1 and TIF1beta as originally identified in the mass spectrometry experiments were also verified by streptavidin pull-down and immunoblotting (FIG. 5). In addition, CoREST, a component of the LSD1/CoREST repressor complex together with HDAC1/2, was also found to interact with biotinylated TR2/TR4, even though it was not originally detected by mass spectrometry. Finally, a previously reported interaction of HDAC3 with TR2 was also confirmed by immunoblotting, although it was not detected by mass spectrometry.

Example 16

Interactions with Natural Abundance Proteins

Figure 6:
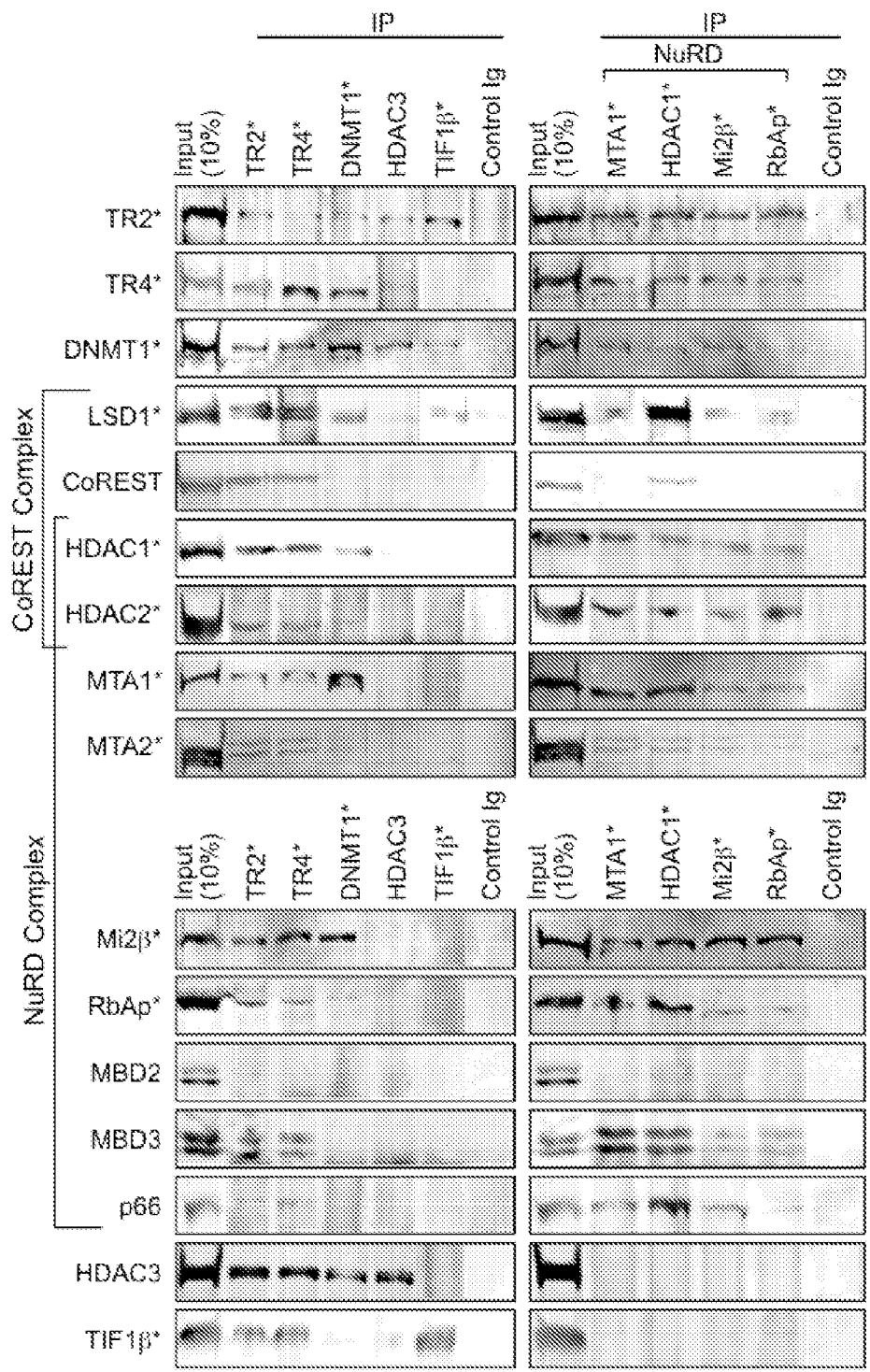
FIG. 6 show the results of immunoblotting analysis of protein interactions in untransformed MEL cells. Nuclear extracts were prepared from untransfected, induced MEL cells and incubated with protein G beads coupled with antibodies against proteins shown at the top of the images, or with a control IgG; 150 µg of nuclear extract protein was used for each lane. Immunoprecipitates with the antibody-coupled beads, and 10% of the input (15 µg protein) were subjected to SDS-PAGE followed by immunoblotting with antibodies against proteins shown to the left of the images. For immunoprecipitation, antibodies against TR2, TR4, DNMT1, HDAC3, and TIF113 were used in the left panels. Antibodies against NuRD subunits (MTA1, HDAC1, Mi2β, and RbAp46/48) were used in the right panels. TR2/TR4-interacting proteins identified by mass spectrometry are indicated by asterisks.

In order to verify that the protein-protein interactions detected by mass spectrometry and immunoblotting following streptavidin-bead purification of tagged TR2/TR4 were genuine and to specifically rule out potentially artifactual interactions that might result from the (aberrantly abundant) expression of tagged TR2/TR4, co-immunoprecipitation assays were performed using nuclear extracts prepared from untransfected MEL cells. TR2, TR4, DNMT1, HDAC3, TIF1beta, LSD1 and NuRD subunits (MTA1, HDAC1, Mi2beta, and RbAp46/48) (FIGS. 6 and 7) were individually immunoprecipitated from nuclear extracts of untransfected MEL cells and then probed on immunoblots to detect potentially interacting proteins. In immune complexes precipitated with either the anti-TR2 or anti-TR4 antibodies, all of the NuRD subunits that were detected by streptavidin pull-down, namely HDAC1/2, MTA1/2, Mi2beta, RbAp46/48, MBD3 and p66, were also detected, whereas MBD2, once again, was not (FIG. 6, left). In the reverse experiments, where antibodies against MTA1, HDAC1, Mi2beta, and RbAp46/48 were used for immunoprecipitation, both TR2 and TR4 were detected in immune complexes (FIG. 6, right). These reciprocally reinforced data confirmed that a bona fide physical interaction takes place between TR2/TR4 and the NuRD complex that contains the MTA1/2, HDAC1/2, Mi2beta, RbAp46/48, MBD3, and p66 subunits.

Figure 7:
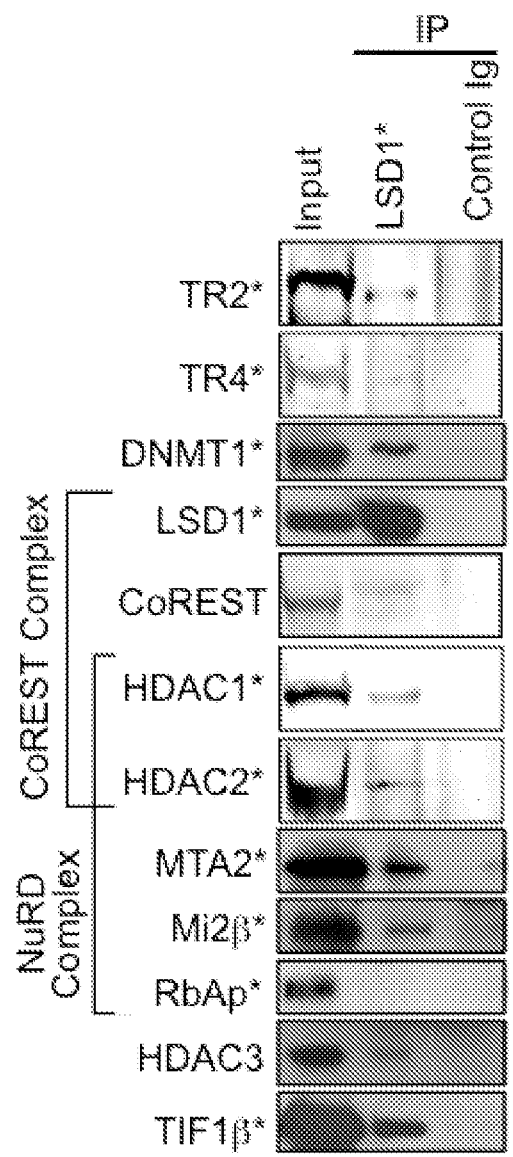
FIG. 7 shows images of proteins that co-immunoprecipitate with LSD1 in MEL cells. Nuclear extracts were prepared from normal, induced MEL cells and incubated with beads coupled with an anti-LSD1 antibody or control IgG. Immunoprecipitates with the anti-LSD1 or control antibody, and 10% of the input were subjected to SDS-PAGE followed by immunoblotting with antibodies against proteins shown on the left. TR2/TR4-interacting proteins identified by mass spectrometry are indicated with asterisks.

DNMT1 and HDAC3 were also co-precipitated in immune complexes formed with either the anti-TR2 or TR4 antibodies (FIG. 6, left). In the reverse experiment using the anti-DNMT1 or HDAC3 antibody for primary immunoprecipitation, both TR2 and TR4 were detected (FIG. 6, left). These results confirmed the in vivo interaction of TR2/TR4 with DNMT1, as well as with HDAC3. TIF1beta was also detected in the complex precipitated with either the anti-TR2 or anti-TR4 antibodies. When the reverse experiment was performed, TR2 was detected in the TIF1beta immunoprecipitate, although TR4 was barely detectable. These results confirmed the in vivo interaction of TR2 with TIF1beta, despite the lack of clear detection of co-precipitated TR4, possibly due to the lower abundance of TR4 compared to TR2 in MEL cells. LSD1/CoREST complex subunits that were detected in the streptavidin purifications were also detected in the TR2 or TR4 immunoprecipitates. In the reverse experiments using an antibody recognizing LSD1 in the immunoprecipitation step, both TR2 and TR4 were detected (FIG. 7). These final co-precipitation results showed that TR2 and TR4 also interact with the LSD1/CoREST complex in vivo.

Example 17

Interactions Between the Co-Repressor Proteins

In addition to the interactions of TR2 and TR4 with potential accessory co-factors, novel as well as known interactions between these co-regulatory proteins were further investigated by co-immunoprecipitation assays. When several NuRD components (MTA1, HDAC1, Mi2beta, or RbAp46/48) were immunoprecipitated with unique antibodies, most of the other NuRD components could clearly be detected in the immune complexes (FIG. 6, right), consistent with the reported subunit structure of the NuRD complex. In the immune complex that was precipitated using an anti-HDAC1 antibody, the CoREST complex subunits, LSD1 and CoREST, were detected (FIG. 6, right), whereas in the immune complex precipitated with an anti-LSD1 antibody, HDAC1, HDAC2 and CoREST were detected (FIG. 7). These data are consistent with the reported subunit structure of the LSD1/CoREST complex.

Among the immune complexes precipitated with the anti-DNMT1 antibody, most of the NuRD subunits (MTA1/2, HDAC1/2, Mi2beta, and RbAp46/48) were co-precipitated and detected by immunoblotting (FIG. 6, left). In the reverse experiments, DNMT1 was also detected in immune complexes that were first precipitated with antibodies against the NuRD subunits MTA1, HDAC1, Mi2beta, or RbAp46/48 (FIG. 6, right). These data clearly demonstrated a novel in vivo interaction between DNMT1 and the NuRD complex. In the DNMT1 immune precipitates, LSD1 was also detected by immunoblotting (FIG. 6, left). In the reverse experiment, DNMT1 was similarly detected in LSD1 immunoprecipitates (FIG. 7), consistent with a previously reported interaction between DNMT1 and LSD1. DNMT1 was also detected in both HDAC3 and TIF1beta immunoprecipitates, whereas, in the DNMT1 immunoprecipitate, HDAC3 was detected but TIF1beta was not (FIG. 6, left). These data also demonstrated novel DNMT1 interactions with TIF1beta, and with HDAC3, despite the failure to detect co-precipitated TIF1beta, possibly due to steric hindrance of a DNMT1 epitope by bound TIF1beta.

In immune complexes precipitated with the anti-LSD1 antibody, most of the NuRD subunits (specifically MTA2, HDAC1/2, and Mi2beta) were detectable by immunoblotting (FIG. 7). In the reverse experiments, LSD1 could be detected among immune complexes precipitated with antibodies recognizing individual NuRD components (MTA1, HDAC1, Mi2beta, and RbAp46/48; FIG. 6, right). These data are consistent with the previously reported interaction between LSD1 and the NuRD complex. In LSD1 immunoprecipitates, TIF1beta and HDAC3 were also detected (FIG. 7). These data demonstrate novel interactions of LSD1 with TIF1beta and with HDAC3.

Example 18

Hypothetical Models for the TR2/TR4 Repressor Complexes

Figure 8:
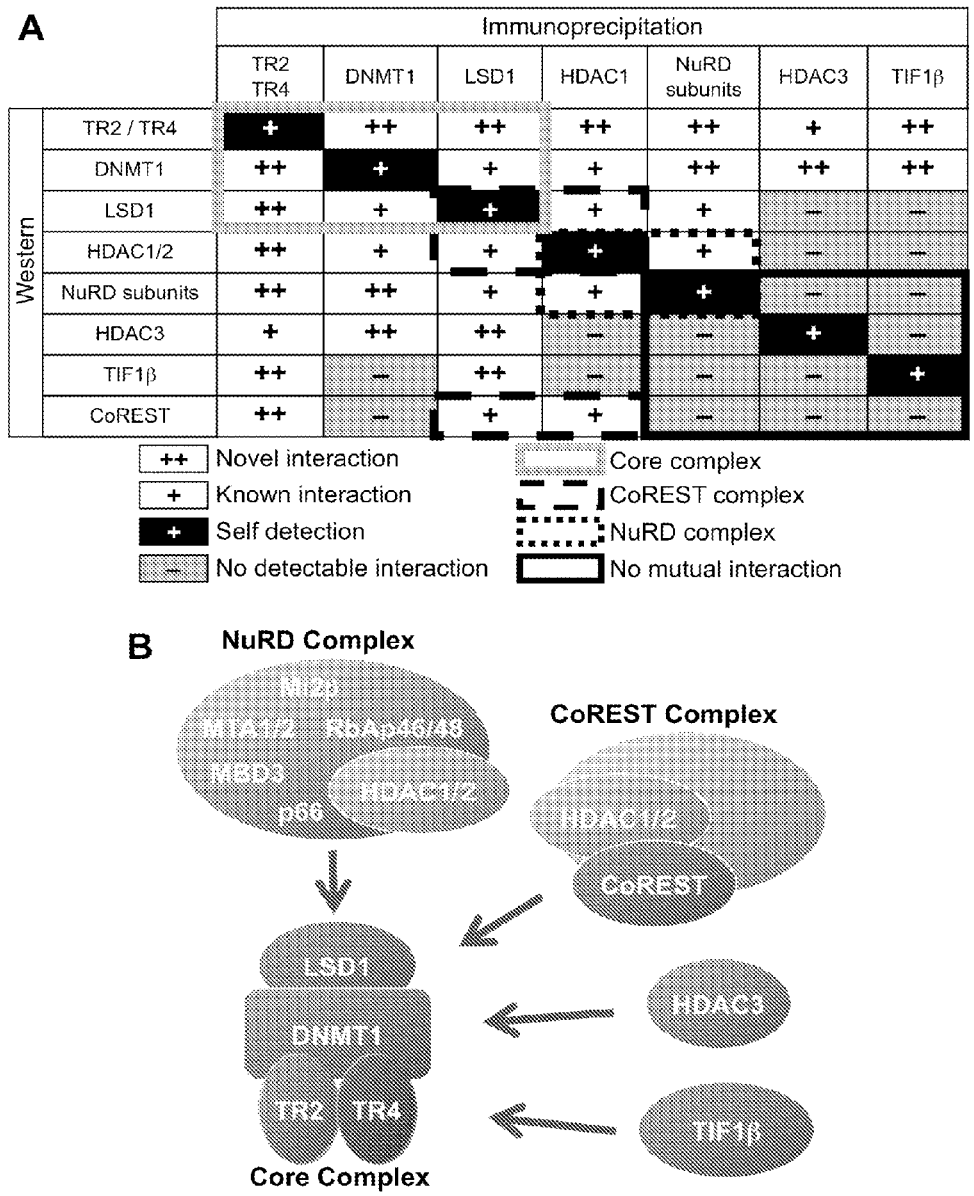
FIG. 8 shows that multiple TR2/TR4 repressor complexes exist in adult erythroid (MEL) cells. Panel A shows a summary of co-immunoprecipitation experiments using normal MEL cells. Novel interactions identified in this study are shown as double plus signs, whereas previously reported interactions are shown as single plus signs. Detection of a protein immunoprecipitated with an antibody against it is shown as white plus signs on a black background as a positive control (i.e., self-detection). Known protein interactions between components of the NuRD and CoREST repressor complexes are shown in rectangles with dotted or broken lines. TR2, TR4, DNMT1, and LSD1 interactions are indicated with a gray rectangle, and comprise a core complex (shown in Panel B). These four core constituents commonly interact with additional proteins, such as HDAC1/2, NuRD components (MTA1/2, Mi2beta, or RbAp46/48), HDAC3, TIF1beta, or CoREST, thus forming larger complexes. However, no mutual interactions between NuRD components (except HDAC1/2), HDAC3, TIF 1beta or CoREST were detected by co-immunoprecipitation (indicated by the black rectangle), suggesting that NuRD, HDAC3, TIF1beta and the CoREST complex bind to the core complex in a mutually exclusive manner, thus forming at least four distinct larger complexes that share the common (TR2+TR4+DNMT1+LSD1) core. Panel B shows a structural model for multiple TR2/TR4 repressor complexes. Based on the results of the co-immunoprecipitation assays reported herein, a structural model is proposed that contains multiple and diverse activities as TR2/TR4 repressor complexes. TR2, TR4, DNMT1, and LSD1 comprise the core negative regulatory silencing complex, to which the NuRD or CoREST complex, HDAC3, or TIF1beta binds in a mutually exclusive manner to form at least four distinct larger complexes that share the core complex.

The results of the co-immunoprecipitation analyses are summarized in FIG. 8A. Based on these, the existence of multiple TR2 and TR4 repressor complexes was postulated. TR2, TR4, DNMT1, and LSD1 were shown to mutually interact with one another in the co-immunoprecipitation assays, suggesting that these four proteins comprise a core complex (FIG. 8B). Most of these four core complex components commonly interact with HDAC1/2, other NuRD components (such as MTA1/2, Mi2beta, or RbAp46/48), CoREST, HDAC3, and TIF1beta, indicating that these proteins can interact with this core complex to form even larger complexes that share the core proteins. Interestingly, no physical interactions among the NuRD signature components (except HDAC1/2), HDAC3, TIF1beta or CoREST were detectable in multiple, independent co-immunoprecipitation experiments (FIG. 8A), suggesting that the interactions of TR2/TR4 with the NuRD complex, with HDAC3, with TIF1beta, or with CoREST are each mutually exclusive and independent associations, and that these proteins form at least four distinct larger complexes that share the core protein group (FIG. 8B).

Example 19

Size Fractionation of Components of TR2/TR4 Repressor Complexes

Figure 9:
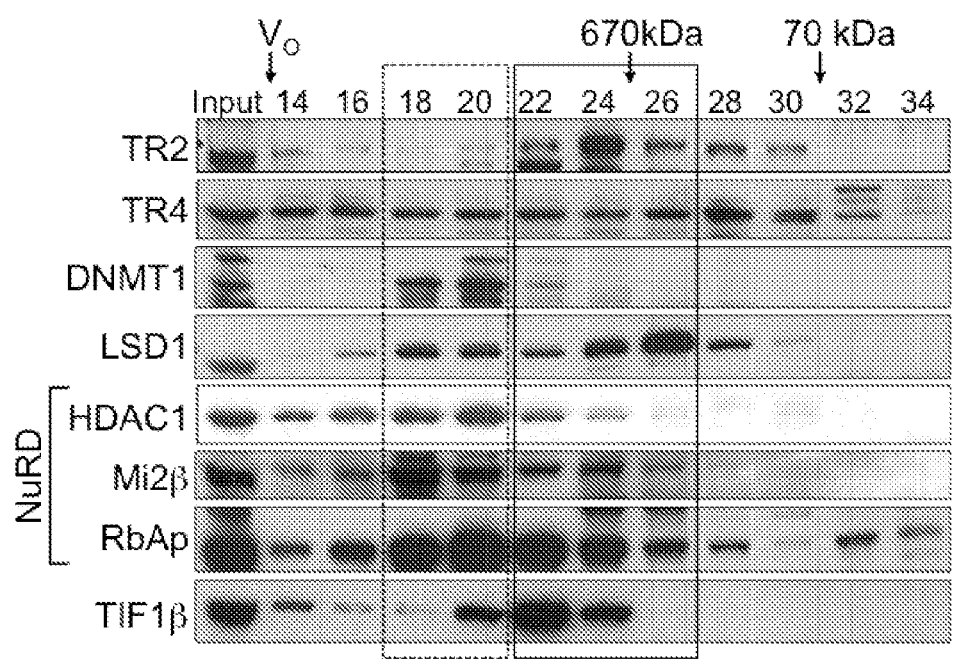
FIG. 9 shows the size fractionation of TR2, TR4 and interacting proteins in nuclear extracts from untransfected, induced MEL cells. Fractions from a Superose 6 gel filtration column were subjected to immunoblotting with antibodies against the proteins shown to the left. Elution positions of molecular weight markers and the void volume ($V_0$) are indicated at the top. Elution peaks of TR2, LSD1, and TIF1β were positioned within fractions 22 through 26 (solid box), while DNMT1 and NuRD components (HDAC1, Mi2β, and RbAp46/48) peaked in fractions 18 through 20 (dotted box) in a higher molecular weight range.

In order to assess how different TR2/TR4-interacting proteins might be differentially partitioned into distinct protein complexes, the fractionation profiles of the proteins was determined by gel filtration on a Superose 6 column (FIG. 9). The elution profile of TR4 is broadly spread almost equally over fractions 14 through 30, whereas TR2, LSD1, and TIF1beta eluted with peaks in fractions 22-26 (solid box in FIG. 9). In contrast, DNMT1 and NuRD components (HDAC1, Mi2beta, and RbAp46/48) peaked in the higher molecular weight range around fractions 18-20 (dotted box), which do not overlap with the peak fractions of TR2. Overall, these results are consistent with the hypothetical model that TR2, TR4, DNMT1, and LSD1 comprise a core complex, which in turn interacts with other proteins (including NuRD components and TIF1beta) to form even larger protein complexes.

Example 20

Figure 10:
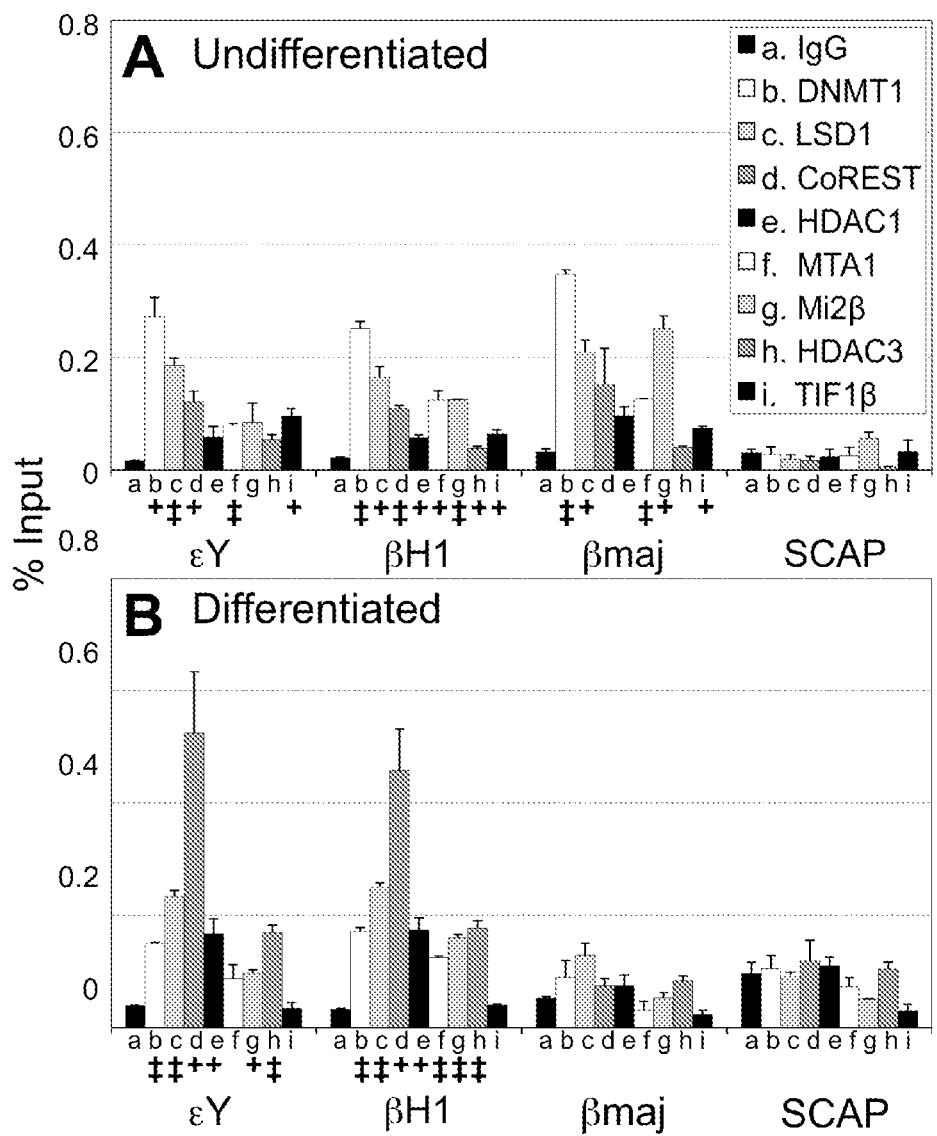
FIG. 10 shows graphs of the binding of TR2/TR4-interacting proteins to the proximal promoter regions of the murine embryonic epsilonY-, betaH1- and adult beta$^{major}$-globin genes in both undifferentiated (Panel A) and differentiated (Panel B) MEL cells analyzed using ChIP assays. As a negative control, binding of the same co-repressors to the promoter of a gene (SCAP) that is transcriptionally active in MEL cells was also examined. Statistically significant enrichment of the co-repressors at the promoters compared to control IgG values is indicated with symbols (+$P<0.05$, ‡$P<0.01$ by Student's t-test). Error bars represent standard errors of the mean (SEM).

Binding of TR2/TR4 Co-Repressors to the Beta-Type Globin Promoters in Adult Erythroid Cells To gain further insight into functional significance of the TR2/TR4-associated co-repressors in beta-type globin gene regulation, their localization based on their own promoters was investigated in adult erythroid (MEL) cells by ChIP assay. MEL cells were grown under conditions that would lead to either continued proliferation (FIG. 10A) or differentiation (with DMSO; FIG. 10B). The data clearly demonstrate that, in undifferentiated MEL cells, DNMT1, subunits of the CoREST complex (LSD1, CoREST, HDAC1), subunits of the NuRD complex (HDAC1, MTA1, Mi2beta), as well as TIF1beta are all recruited to both the embryonic (epsilonY and betaH1) as well as the adult beta$^{major}$-globin promoters, whereas HDAC3 is recruited only to the epsilonY-globin promoter (FIG. 10A). In contrast, localization of these co-repressors to the promoters of a gene (SCAP) highly transcribed in MEL cells is essentially undetectable. These data imply that, in undifferentiated cells, the adult beta-globin gene is, in fact, actively repressed even in cells poised to transcribe the gene, although the nature of other DNA binding factors that attract these multiple co-repressors to the inactive, but poised adult beta-globin gene remain to be discovered.

Interestingly, upon terminal differentiation, almost all of these co-repressors dissociate specifically from the adult beta$^{major}$-globin promoter (FIG. 10B). In contrast, all these co-repressors except TIF1beta remain bound to the embryonic globin promoters, although association of DNMT1, MTA1, and Mi2beta is somewhat reduced compared to uninduced cells, suggesting differential roles for each co-repressor in embryonic globin gene silencing during erythroid differentiation. These data suggest that the specific binding of TR2/TR4 to the conserved DR sequences in the embryonic globin promoters cause persistent association of the TR2/TR4-interacting co-repressors to the embryonic globin promoters through terminal differentiation, thereby fulfilling the TR2/TR4-induced silencing of the embryonic globin genes.

Previously, it was shown in undifferentiated murine adult erythroid cells that active histone marks [histone H3 and H4 acetylation, and H3 lysine 4 (H3K4) methylation] are only modestly enriched even on the adult beta-globin promoter, and, after differentiation, these active marks will become highly enriched specifically on the adult, but not on the embryonic, beta-type globin promoters. It was also reported that, in human adult hematopoietic progenitor cells, the promoter DNA of both the fetal gamma- and adult beta-globin genes are highly methylated, and, during differentiation, the adult beta-globin promoter DNA specifically undergoes extensive demethylation, another hallmark of gene activation, but the fetal gamma-globin promoter does not. TR2/TR4-interacting co-repressors include enzymes that can remove or cancel all of these epigenetic activation marks, namely HDAC1/2/3, methyl-H3K4 demethylase LSD1, and DNMT1. The differentiation-dependent specific dissociation of these enzymes from the adult beta-globin promoter shown here may constitute the key underlying mechanism for generation of the active chromatin structures exclusively on the adult beta-globin genes in adult erythroid cells, causing the high-level transcription of the adult genes as well as the silencing of embryonic or fetal beta-type globin genes.

Part B

Example 21

Ex Vivo Differentiation of Purified Human CD34+ Cells

Cryopreserved vials of purified human CD34+ cells, which were isolated from peripheral blood of healthy donors after mobilization with granulocyte colony-stimulating factor, were purchased from the Fred Hutchinson Cancer Research Center. The cells were grown and differentiated ex vivo into the erythroid lineage in 14 days by a two-phase culture method reported previously (Cui et al., 2011, *Mol. Cell. Biol.,* 31:3298-3311; Giarratana et al., 2005, *Nat. Biotechnol.,* 23:69-74). Cell number and viability were determined with a hemocytometer by trypan blue staining Tranylcypromine (Tocris Bioscience) at 50 mM in water was added to the culture medium on day 4 through day 14. Cell morphology was examined by staining cytospins with a Wright-Giemsa stain (Sigma-Aldrich). Hemoglobin synthesis was examined by acid benzidine staining as previously described (Orkin et al., 1975, *PNAS USA,* 72:98-102).

Example 22

Flow Cytometry

For cell surface marker analysis, cells were stained with phycoerythrin (PE)-Cy7-conjugated anti-CD34 (eBioscience), PE-conjugated anti-CD71 (eBioscience), and PE-Cy5-conjugated antiglycophorin A (BD Biosciences) antibodies. For cytoplasmic HbF analysis, cells were fixed in 0.05% glutaraldehyde for 10 min, permeabilized in 0.1% Triton X-100 for 5 min, and then stained with allophycocyanin-conjugated anti-HbF antibody (Invitrogen). Stained cells were analyzed with the FACSCanto II (BD Biosciences).

Example 23

Western Blotting

Cells were lysed in a Laemmli sample buffer and subjected to SDS-PAGE. Proteins were then transferred to a nitrocellulose membrane (Li-Cor) and probed with an antibody against LSD1 (Abcam, ab17721), histone H3 (Abcam, ab1791), or dimethyl H3K4 (Abcam, ab19946), and fluorescence-conjugated secondary antibodies (Li-Cor). Proteins were visualized and quantified with the Odyssey Infrared Imaging System (Li-Cor). For quantification results, averages of three or four biological replicates are presented.

Example 24

ChIP Assay

ChIP assay was performed essentially as described previously (Cui et al., supra). For LSD1 analysis, ethylene glycol bis(succinimidyl succinate) was used as an additional cross-linker to formaldehyde. The anti-LSD1 antibody or a mouse monoclonal anti-dimethyl H3K4 antibody (Millipore, 05-1338) was used for immunoprecipitation. Precipitated DNA was quantified by real-time quantitative PCR assay with primers for human epsilon-, gamma-, and beta-globin promoter sequences (Cui et al., supra), as well as primes for an intergenic region between epsilon- and Ggamma-globin genes as a negative control (5'-TCC CAC TCT GTG GGT TGT CTG TTT-3' (SEQ ID NO:11) and 5'-CCC TTC TAC ACA TTG GCT TAG GAA AGG-3' (SEQ ID NO:12)). Averages of two to four independent immunoprecipitations are presented.

Example 25

Hemoglobin Analysis by HPLC

Cells were lysed and analyzed for hemoglobin composition by the B10-Rad Variant II Hemoglobin Testing System equipped with an ion-exchange HPLC column (Hercules). Averages of three to five biological replicates are presented.

Example 26

RT-qPCR Assay

Expression of the genes for human gamma- and beta-globins, LSD1, mouse alpha-globin, and 18S rRNA was determined by RT-qPCR assay as described previously (Cui et al., supra). The abundance of each transcript was calculated based on the threshold cycle value and the amplification efficiency, experimentally determined for each primer pair, and then normalized to the abundance of 18S rRNA transcript as an internal control. All the primer pairs except for 18S rRNA were designed to span introns. Primer sequences are following: human gamma-globin, 5'-GAT GCC ATA AAG CAC CTG GAT G-3' (SEQ ID NO:13) and 5'-TTG CAG AAT AAA GCC TAT CCT TGA-3' (SEQ ID NO:14); human beta-globin, 5'-AAC TGT GTT CAC TAG CAA CCT CAA-3' (SEQ ID NO:15) and 5'-GAG TGG ACA GAT CCC CAA AGG A-3' (SEQ ID NO:16); LSD1,5'-TGG CCA TTC TCA AAG GGA TT-3' (SEQ ID NO:17) and 5'-CAG CAC GCC AAC GAG ACA-3' (SEQ ID NO:18); mouse alpha-globin, 5'-CCC GGT GCC TTG TCT GCT-3' (SEQ ID NO:19) and 5'-GTG AAA TCG GCA GGG TGG-3' (SEQ ID NO:20); and 18S rRNA, 5'-ACC GCA GCT AGG AAT AAT GGA-3' (SEQ ID NO:21) and 5'-GCC TCA GTT CCG AAA ACC A-3' (SEQ ID NO:22).

Example 27

Expression of LSD1 shRNA by Lentiviral Vector

A pLKO.1-puro lentiviral vector to express the LSD1 shRNA and a puromycin resistance gene was purchased from Sigma-Aldrich (TRCN0000046070), and the control empty vector was generated by removing a region (between EcoRI and NdeI sites) containing the hairpin sequence. Lentiviral particles were generated by transfecting the vectors into a packaging cell line. Cells were exposed to the viruses on day 4 of the culture for 24 hours, and then to 1 μg/ml puromycin on day 6 through day 14 for selection of infected cells.

Example 28

Tranylcypromine Administration to Mice

Tranylcypromine, dissolved in saline, was administrated to transgenic mice harboring a yeast artificial chromosome containing a whole human β-type globin locus (Tanimoto et al., 2000, Genes Dev., 14:2778-94; Tanabe et al., 2007, EMBO J., 26:2295-2306) by subcutaneous injection at a dose of 3 or 10 mg/kg body weight per day, 5 days a week. Control mice were injected with saline only. After 4 weeks of injections, bone marrow cells were harvested for RTqPCR analysis for expression of the genes for human gamma- and beta-globins, and mouse alpha-globin as an internal control. Three or four mice were used for each experimental condition.

Example 29

Statistical Analysis

Student's t-test was used for all the statistical analyses, where asterisks indicate significant difference (*, $P<0.05$; **, $P<0.01$). Error bars represent SEM (standard error of the mean).

Example 30

Discussion

To gain insight into the possible role of LSD1 in human beta-type globin gene regulation, the expression of LSD1 and its possible association with the beta-type globin promoters was examined in primary human erythroid cells that had been differentiated ex vivo from purified CD34+ hematopoietic progenitors (Giarratana et al., supra). Synchronized differentiation toward the erythroid lineage can be achieved by adding multiple cytokines to the cultures, and erythroid differentiation was confirmed by morphological and detailed biochemical analysis. Most of the cells appeared to be proerythroblasts by day 8 of differentiation, and, by day 11, approximately 30% of the cells had the appearance of polychromatic erythroblasts (FIG. 11(a)). By differentiation day 14, an average of 26% of the cells had undergone enucleation, which is the ultimate hallmark of terminal erythroid differentiation. The morphological change in the cells during differentiation was accompanied by hemoglobin accumulation as indicated by acid benzidine staining, which increased from 44% of the cells being positive on day 8 to 92% positive by day 14 (FIG. 11(a)). Erythroid differentiation of the cells was also confirmed by flow cytometry. Cells expressing CD34, the marker for hematopoietic progenitors, steadily declined from 97% on day 0 to 0.8% on day 14, whereas cells expressing both the transferrin receptor (CD71) and glycophorin A (GPA), representing a mature erythroid population, increased from 16% on day 4 to 96% on day 14 (FIG. 11(b)). Western blotting showed that LSD1 protein was expressed at a relatively constant level during this differentiation period (FIG. 11(c)). By chromatin immunoprecipitation (ChIP) assay, LSD1 binding to the embryonic epsilon- and fetal gamma-globin promoters was readily detected in immature erythroid cells (FIG. 11(d)), implicating a role for LSD1 in the regulation of these genes. LSD1 was also detected at the adult beta-globin promoter, but as the cells matured during the differentiation process, LSD1 binding to all of the beta-type globin gene promoters diminished.

Figure 12B:
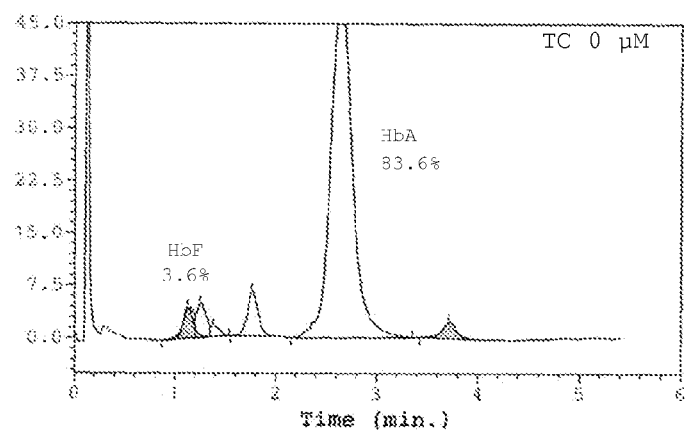
Figure 12B:
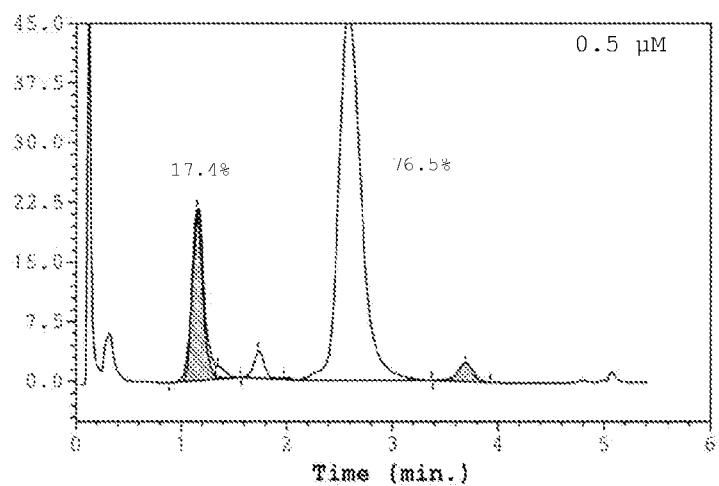
Figure 12B:
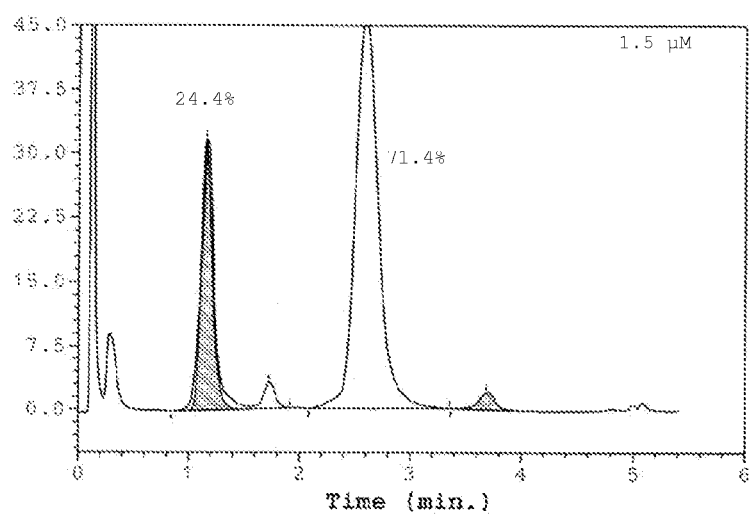

Tranylcypromine (TC) is a monoamine oxidase inhibitor that has been used clinically as an antidepressant since 1960, and was shown to be a potent inhibitor of LSD1 with a half maximal inhibitory concentration ($IC_{50}$) of less than 2 μM (Lee et al., 2006, Chem. Biol., 13:563-567). In order to investigate what role, if any, LSD1 might play in beta-type globin gene regulation, the effects of TC on primary human erythroid cells was examined. Cells in the ex vivo differentiation culture were exposed to TC at concentrations of 0.5, 1.5 or 5 μM on day 4 through day 14. TC administration at 0.5 or 1.5 μM did not affect proliferation or viability of the cells, but 5 μM of TC reduced cell proliferation without affecting viability (FIG. 12(a)). The synthesis of fetal (HbF) and adult (HbA) hemoglobins, consisting of either alpha- plus gamma-, or alpha- plus beta-chains, respectively, was also examined by high performance liquid chromatography (HPLC) after 14 days of differentiation culture. HbF synthesis was significantly enhanced by TC, going from 4.6% of total hemoglobin in (untreated) control cells to 13%, 20% or 31% (on average) in cells treated with 0.5, 1.5 or 5 μM TC, respectively (FIG. 12(b), 12(c); within or slightly exceeding the prescribed clinical dosages for the treatment of depression). Flow cytometric analysis demonstrated that the HbF inductive effect was both pancellular and dose-dependent on TC concentration (FIG. 12(d)). Reverse transcription and quantitative real-time PCR (RT-qPCR) analysis showed corresponding induction of fetal gamma-globin mRNA after TC treatment up to 9.4-fold by day 14 (FIG. 12(e)), which significantly exceeds the reported effects of current gamma-globin-inducing medications (such as HU or 5-azacytidine) on gamma-globin gene expression in cultured primary human erythroid cells (Mabaera et al., 2008, Blood, 111:411-20; Bradner et al., 2010, PNAS USA, 107: 12617-22). Collectively, the dose dependent, robust induction of fetal gamma-globin synthesis by TC suggests a critical role for LSD1 in the silencing of the fetal gamma-globin genes in adult erythroid cells, and indicates that TC may be effectively applied to the treatment of beta-globin disorders as a novel fetal hemoglobin inducing agent, since the effective concentration for gamma-globin induction is within the range of therapeutic concentrations that are currently used for the treatment of major depressive disorder. The effects of TC administration on erythroid surface marker expression was also examined by flowcytometric analysis, and it was found that it causes slight to moderate reduction in the cell population positive for both CD71 and GPA in a dose dependent manner (FIG. 12(f)), which is consistent with the role of LSD1 in erythroid differentiation.

To address the mechanism by which TC elicited these quite dramatic HbF inductive effects, the effect of TC administration on histone H3 lysine 4 (H3K4) dimethylation was next examined in the differentiating erythroid cells to determine whether or not LSD1 inhibition actually accounts for the fetal γ-globin induction by TC. Initially, to quantify global H3K4 dimethylation, total cell extracts prepared on day 8, 11, and 14 of the ex vivo differentiation culture in the absence of TC treatment were subjected to Western blotting with an antibody recognizing either total histone H3 or dimethyl H3K4 to determine its relative abundance during erythroid differentiation. The data showed a rapid global increase of dimethyl H3K4 during terminal differentiation (FIG. 13(a)). TC treatment enhanced global H3K4 dimethylation in a dose dependent manner, confirming the inhibitory effect of TC on H3K4 demethylase activity of LSD1 in differentiating erythroid cells (FIG. 13(b)). H3K4 dimethylation at the beta-type globin gene promoters was then examined during differentiation by ChIP assays. In immature erythroid cells on day 8, dimethyl H3K4 was not detectable at either of the globin promoters examined, but toward terminal differentiation, it rapidly accumulated at both the fetal gamma- and adult beta-globin promoters (FIG. 13(c)), potentially due to the dissociation of LSD1 from these promoters during the terminal differentiation process (FIG. 11(d)). TC treatment enhanced H3K4 dimethylation at the gamma-globin promoter (FIG. 13(d)), consistent with the hypothesis that TC induces fetal gamma-globin synthesis by inhibiting LSD1 and thereby enhancing accumulation of dimethyl H3K4 at the gamma-globin promoter.

Figure 14C:
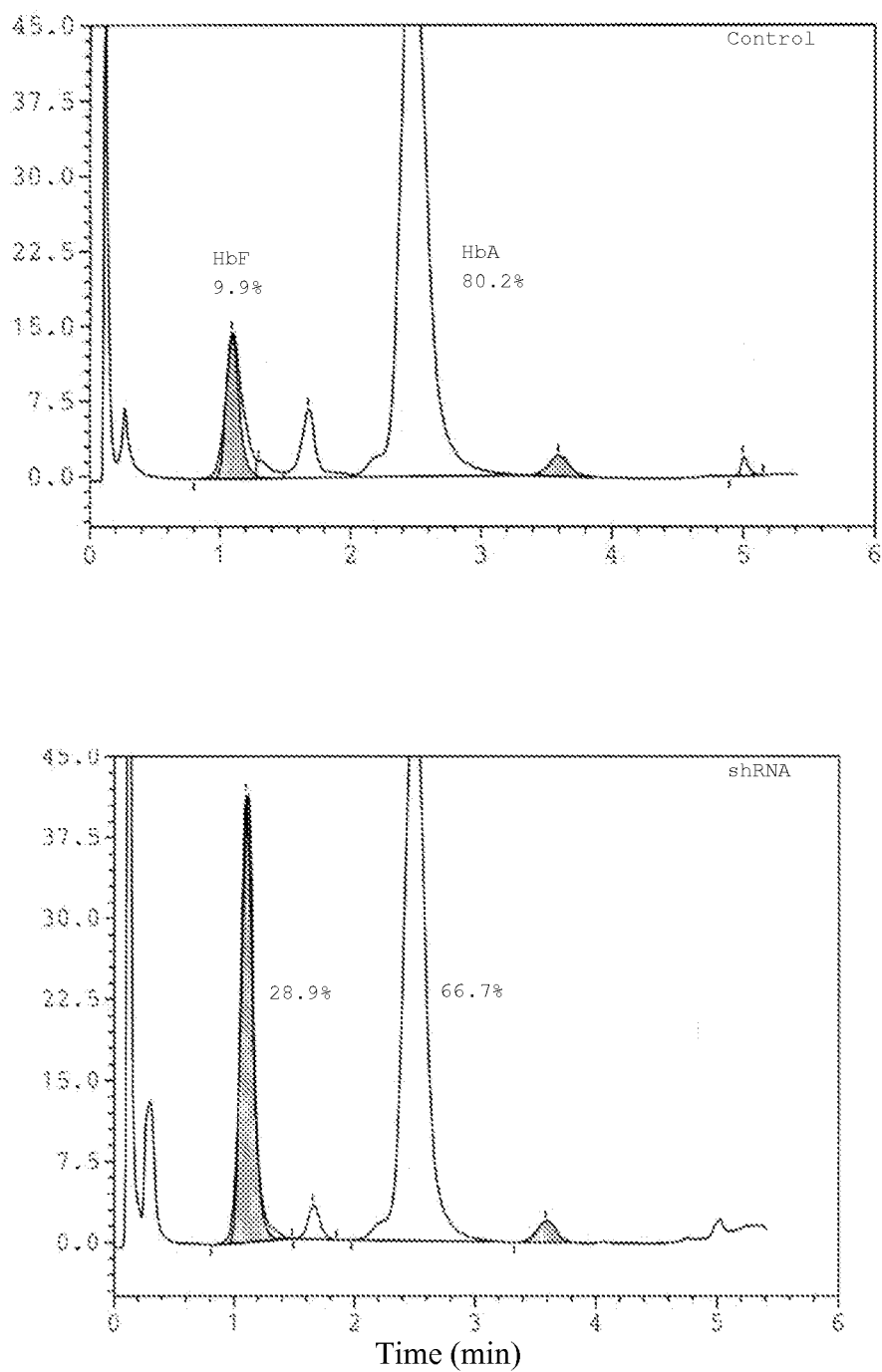

In order to further define the role of LSD1 in fetal gamma-globin silencing as well as to address the mechanism of the fetal gamma-globin induction using an alternative strategy, the effect of lentivirus-mediated knockdown of LSD1 on fetal gamma-globin synthesis was examined. Primary human CD34+ cells were infected 4 days after erythroid differentiation induction with a lentivirus expressing a short-hairpin RNA (shRNA) containing a human 21-nucleotide LSD1 mRNA sequence, and then treated with puromycin to select for infected cells. The abundance of LSD1 mRNA in the cells infected with the shRNA virus was reduced to 45% and 23% on days 11 and 14, respectively, as compared to cells infected with a control virus (FIG. 14(a)). Correspondingly, the abundance of LSD1 protein was reduced by infection with the shRNA virus to 31% or 13% on days 11 and 14, respectively, as compared to control infected cells (FIG. 14(b)). Growth or viability of the cells was not significantly affected by LSD1 knockdown within this time frame. HPLC analysis revealed that HbF synthesis on day 14 was significantly enhanced, from 10% to 31%, by LSD1 knockdown (FIGS. 14(c), (d)), whereas RT-qPCR analysis showed a corresponding 3-fold induction of fetal gamma-globin mRNA (FIG. 14(e)). These results phenocopy those achieved by TC inhibition of LSD1 activity, and underscore the critical role that LSD1 plays in fetal gamma-globin silencing in adult erythroid cells. When taken together with the demonstrated TC-induced enhancement of H3K4 dimethylation at the fetal gamma-globin promoter, both experiments support the notion that TC induces fetal gamma-globin synthesis through the inhibition of LSD1 activity.

Finally, the effects of TC on gamma-globin gene expression were tested in transgenic mice harboring a yeast artificial chromosome containing the whole human beta-type globin locus (Tanimoto et al., supra; Tanabe et al., supra) by administering two different doses of TC (3 or 10 mg/kg body weight per day) by subcutaneous injection, 5 days a week for 4 weeks. Expression of the human gamma-globin gene in bone marrow cells was induced in a dose dependent manner by TC by about 3-fold as compared to control mice (FIG. 14(f)), even though in the mouse trans-acting factor milieu, the human gamma-globin gene behaves essentially as an embryonic globin gene, and is normally strongly silenced in the adult stage, especially within the context of the whole intact genomic locus (Tanabe et al., supra; Sankaran et al., 2009, Nature, 460:1093-7). Human beta-globin gene expression was not significantly affected by TC administration (FIG. 14(f)). The magnitude of gamma-globin induction in the mouse model in vivo by TC compares favorably to, or exceeds, all previously reported inducing effects of 5-aza-2'-deoxycytidine or HU in comparable transgenic mouse models (Xu et al., 2011, Science, 334:993-6; Meiler et al., 2011, Blood, 118:1109-12). The administration of TC was well tolerated by mice and did not exhibit any signs of toxic effects on hematological or other systems, although anecdotally the mice appeared to be much more active than their untreated counterparts.

This study demonstrates that LSD1 plays a critical role in adult-stage fetal gamma-globin silencing and thus can be a novel therapeutic target for fetal gamma-globin induction, and that a currently prescribed (for other use) pharmacological inhibitor, TC, can actually enhance gamma-globin gene expression in primary human erythroid cells as well as in an in vivo mouse model. These findings qualify LSD1 as an extraordinary and novel therapeutic target for beta-globin disorders in that its potent inhibitor, TC, has been widely used for five decades as a human clinical medicine with manageable side effects. TC exerts an antidepressant effect by inhibiting monoamine oxidases and thereby elevating catecholamine and serotonin levels, and does not appear to have cytotoxic or mutagenic effects, in contrast to current gamma-globin inducing medications. Therefore, TC may serve as a direct or lead compound for developing a safer gamma-globin inducing agent with a novel, well characterized mechanism of action as its basis, which may complement or even supersede medications currently prescribed for the treatment of beta-globin disorders.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A method of screening for compounds that stimulate expression of a gamma-globin gene, wherein said method comprises the steps of:
contacting a recombinant non-erythroid host cell with a test compound, wherein the recombinant non-erythroid host cell comprises an exogenous nucleic acid sequence encoding a DNA methyltransferase I (DNMT1) polypeptide and a nucleic acid sequence encoding a detectable polypeptide operably linked to a human gamma-globin gene promoter; and
measuring the amount of the detectable polypeptide in the presence and absence of the test compound, wherein an increase in the amount of the detectable polypeptide in the presence of the test compound compared to the amount of the detectable polypeptide in the absence of the test compound identifies a selected test compound as a compound that stimulates expression of the gamma-globin gene.

2. A method of screening for compounds that stimulate expression of a gamma-globin gene, wherein said method comprises the steps of:
contacting a recombinant non-erythroid host cell with a test compound, wherein the recombinant non-erythroid host cell comprises an exogenous nucleic acid sequence encoding the lysine-specific histone demethylase (LSD)-1 polypeptide and a nucleic acid sequence encoding a detectable polypeptide operably linked to a human gamma-globin gene promoter; and
measuring the amount of the detectable polypeptide in the presence and absence of the test compound, wherein an increase in the amount of the detectable polypeptide in the presence of the test compound compared to the amount of the detectable polypeptide in the absence of the test compound identifies a selected test compound as a compound that stimulates expression of gamma-globin gene.

3. A method of screening for compounds that de-repress a human gamma-globin gene, wherein said method comprises the steps of:
contacting a recombinant non-erythroid host cell with a test compound, wherein the recombinant non-erythroid host cell comprises an exogenous nucleic acid sequence encoding a TR2 polypeptide, an exogenous nucleic acid sequence encoding a TR4 polypeptide, an exogenous nucleic acid sequence encoding a DNMT1 polypeptide or a LSD-1 polypeptide or both, and a nucleic acid sequence encoding a detectable polypeptide operably linked to a human gamma-globin gene promoter, and optionally, one or more nucleic acids encoding a nucleosome remodeling and deacetylase (NuRD) complex, a CoREST complex, an HDAC3 polypeptide, and a transcriptional intermediary factor (TIF)-1 beta polypeptide; and
measuring an amount of the detectable polypeptide in the presence and absence of the test compound, wherein an increase in the amount of the detectable polypeptide in the presence of the test compound compared to the amount of the detectable polypeptide in the absence of the test compound identifies a selected test compound as a compound that de-represses the human gamma-globin gene.

4. The method of claim 1, 2 or 3, wherein the compounds are selected from the group consisting of small molecules, polypeptides, synthetic compounds, naturally-occurring compounds, antibodies, antigen-binding fragment, and antigens.

5. The method of claim 1, 2 or 3, wherein at least two of the nucleic acid sequences in claim 1, 2 or 3 is heterologous to the recombinant cell.

6. The method of claim 1, 2 or 3, wherein the detectable polypeptide is selected from the group consisting of luciferase, beta-glucuronidase (GUS), beta-galactosidase, and chloramphenicol acetyltransferase (CAT).

7. A method of treating a beta-globin disorder in an individual in need of such treatment, comprising the steps of:
administering an effective amount of a compound that inhibits LSD-1 to an individual suffering from a beta-globin disorder, wherein the effective amount of the compound that inhibits LSD-1 is an amount that de-represses the human gamma-globin gene; and
detecting expression of the gamma-globin gene in the individual, thereby treating the beta-globin disorder.

8. The method of claim 7, wherein the compound that inhibits LSD-1 is selected from the group consisting of a tranylcypromine, a polyamine, and a 2-PCPA.

9. The method of claim 7, wherein the beta-globin disorder is selected from the group consisting of sickle cell disease and beta-thalassemia.

10. A method of treating a beta-globin disorder in an individual in need of such treatment, comprising the steps of:

identifying an individual having a beta-globin disorder; and administering an effective amount of a compound that inhibits LSD-1 to an individual suffering from a beta-globin disorder, wherein the effective amount of the compound that inhibits LSD-1 is an amount that de-represses the human gamma-globin gene, thereby treating the beta-globin disorder.

11. The method of claim 10, wherein the compound that inhibits LSD-1 is selected from the group consisting of a tranylcypromine, a polyamine, and a 2-PCPA.

12. The method of claim 10, wherein the beta-globin disorder is selected from the group consisting of sickle cell disease and beta-thalassemia.

* * * * *